US010930376B2

United States Patent
Rentas et al.

(10) Patent No.: US 10,930,376 B2
(45) Date of Patent: Feb. 23, 2021

(54) PATIENT TEST DATA PROCESSING SYSTEM AND METHOD

(71) Applicant: GOODMARK MEDICAL (INTERNATIONAL) LTD., Edinburgh (GB)

(72) Inventors: Nestor Rentas, Orlando, FL (US); Sheila Coffman, Sanford, FL (US); Gregg Flynn, Deltona, FL (US); Marryat Stevens, Surrey (GB); Steven Hall, Falkirk (GB); Christopher Carter, Edinburgh (GB); Neil Farish, Edinburgh (GB)

(73) Assignee: Goodmark Medical (International) Limited, Edinburgh (GB)

( * ) Notice: Subject to any disclaimer, the term of this patent is extended or adjusted under 35 U.S.C. 154(b) by 1156 days.

(21) Appl. No.: 14/462,722

(22) Filed: Aug. 19, 2014

(65) Prior Publication Data

US 2015/0051922 A1 Feb. 19, 2015

Related U.S. Application Data

(60) Provisional application No. 61/867,324, filed on Aug. 19, 2013.

(30) Foreign Application Priority Data

Sep. 24, 2013 (GB) .................................... 1316921

(51) Int. Cl.
*G16H 10/60* (2018.01)
*G16H 10/40* (2018.01)

(52) U.S. Cl.
CPC ............. *G16H 10/40* (2018.01); *G16H 10/60* (2018.01)

(58) Field of Classification Search
CPC ....................................................... G16H 10/60
See application file for complete search history.

(56) References Cited

U.S. PATENT DOCUMENTS

| 5,214,761 | A  | * | 5/1993 | Barrett | G06F 13/102 |
|---|---|---|---|---|---|
| | | | | | 710/64 |
| 2002/0128861 | A1 | * | 9/2002 | Lau | G16H 70/20 |
| | | | | | 705/2 |
| 2004/0078224 | A1 | * | 4/2004 | Schramm-Apple | ......................... |
| | | | | | G06F 19/324 |
| | | | | | 705/2 |
| 2005/0055242 | A1 | * | 3/2005 | Bello | G06Q 50/22 |
| | | | | | 705/2 |
| 2005/0273367 | A1 | * | 12/2005 | Nourie | G06Q 10/10 |
| | | | | | 705/3 |
| 2008/0021730 | A1 | * | 1/2008 | Holla | G06F 19/322 |
| | | | | | 705/2 |

(Continued)

*Primary Examiner* — John A Pauls
(74) *Attorney, Agent, or Firm* — Schwegman Lundberg & Woessner, P.A.

(57) ABSTRACT

A method and system is disclosed for receiving patient test data from a point of care computer, identifying additional required data missing from the patient test data according to electronic health record provider requirements, transmitting an indication to the point of care computer of the additional required data to be input by an operator of the point of care computer; receiving operator input data from the operator; and adding the input data to the patient test data to store complete patient test data.

26 Claims, 14 Drawing Sheets

(56) References Cited

U.S. PATENT DOCUMENTS

| | | | |
|---|---|---|---|
| 2009/0103916 A1* | 4/2009 | Dolan, III | H04L 41/0213 398/9 |
| 2012/0310872 A1* | 12/2012 | Anderson | G06Q 40/06 706/46 |
| 2012/0323591 A1* | 12/2012 | Bechtel | G06F 19/321 705/2 |
| 2013/0325515 A1* | 12/2013 | Nikolova-Simons | G06F 19/3431 705/3 |

* cited by examiner

PATIENT TEST DATA PROCESSING SYSTEM AND METHOD

CLAIM OF PRIORITY

This application claims the benefit of priority to United Kingdom Patent Application Serial No. GB 1316921.4, filed Sep. 24, 2013 and claims priority to U.S. Provisional Patent Application Ser. No. 61/867,324, filed Aug. 19, 2013, which are hereby incorporated by reference in their entirety.

FIELD OF THE INVENTION

The present invention generally relates to a data processing system and method for processing patient test data and for determining regulatory compliance.

BACKGROUND OF THE INVENTION

Point-of-care testing (POCT) is medical testing at or near the site of patient care. The driving notion behind POCT is to bring the test conveniently and immediately to the patient. This increases the likelihood that the patient, physician, and care team will receive the results quicker, which allows for immediate clinical management decisions to be made. POCT includes: blood glucose testing, blood gas and electrolytes analysis, rapid coagulation testing, rapid cardiac markers diagnostics, drugs of abuse screening, urine strips testing, pregnancy testing, faecal occult blood analysis, food pathogens screening, haemoglobin diagnostics, infectious disease testing and cholesterol screening.

POCT is often accomplished through the use of transportable, portable, and handheld instruments (e.g., blood glucose meter, nerve conduction study device) and test kits. Small bench analysers or fixed equipment can also be used when a handheld device is not available—the goal is to collect the specimen and obtain the results in a very short period of time at or near the location of the patient so that the treatment plan can be adjusted as necessary before the patient leaves. Cheaper, smaller, faster, and smarter POCT devices have increased the use of POCT approaches by making it cost-effective for many diseases, such as diabetes, carpal tunnel syndrome (CTS) and acute coronary syndrome.

There is a desire to get output of a POCT device made available immediately within an electronic medical record. The advantage of such integration into electronic medical health records is that results can be shared instantaneously with all members of the medical team through the software interface enhancing communication by decreasing turn-around time (TAT). Also, errors caused by manual input are avoided.

One of the challenges accompanying the use of POCT is the plethora of devices and tests which brings with it a high degree of complexity in integrating the POCT devices due to the lack of any agreed standard for data output from such devices. To further complicate matters, there are a number of electronic health record providers, each with its own requirements and non-standard data format. On top of this, the use of POCT is subject to strict medical regulatory compliance requirements.

SUMMARY OF THE INVENTION

One aspect of the invention provides a method and a point of care computer in which patient test data is received for a patient test from a point of care device over a device interface; the patient test data is transmitted to a remote server system over a network; data identifying additional required data is received; a display interface is generated on a display indicating the additional required data; operator input data is received in response from a user input device; and the operator input data is transmitted to the server system over the network.

This aspect of the invention can also provide a method and a server system to process patient test data from at least one point of care device in which patient test data is received from a point of care computer from a point of care interface, the point of care computer receiving the patient test data from at least one point of care device; additional required data missing from the patient test data is identified according to electronic health record provider requirements; the point of care interface is used to transmit an indication to the point of care computer of the additional required data to be input by an operator of the point of care computer; operator input data is received from the point of care computer; and the operator input data is added to the patient test data to form and store complete patient test data.

This aspect of the invention ensures that all of the data required for a patient test record in an electronic health record are captured by identifying additional required data not provided in the output of the point of care device, prompting the operator to input the additional required data on a point of care computer, and combining the data to form a complete patient test record which can be made available for input to an electronic health record.

Another aspect of the invention provides a method and server system for determining regulatory compliance for point of care patient testing by operators using point of care devices, wherein operator data for a plurality of point of care device operators is stored in an operator data store, the operator data including information for each operator indicating qualifications for the point of care devices and/or types of patient testing; point of care device data for a plurality of point of care devices is stored in a device data store, the point of care device data including records of quality control tests and/or maintenance data for each point of care device; regulatory compliance requirement data on requirements for medical patient testing regulatory compliance is stored in a regulatory compliance data store; patient test data and data identifying the operator and the point of care device is received and stored in a patient test data store; and the stored data is processed using the stored operator data, point of care device data, and regulatory compliance requirement data to determine if the patient test is regulatory compliant, and to indicate in the patient test data store whether or not the patient test data is regulatory compliant.

In this aspect of the invention the problem of regulatory compliance is addressed by capturing and storing operator qualification information and device quality control test or maintenance data and when patient test data is received, regulatory compliance can be checked by reference to the stored operator qualification information and device quality control test or maintenance data and stored regulatory compliance requirement data. The patient test data can hence be flagged if it is determined that the device and/or operator failed the compliance test and the patient test data can either be passed flagged accordingly to an electronic health record provider for insertion into the patient's electronic health record, or the patient test data can be blocked or prevented from being sent to the electronic health record provider. In this way, the method and system can keep a record of regulatory compliance for a plurality of point of care devices and a plurality of operators. Reports can be generated when required identifying point of care devices, point of care computers, point of care facilities and operators.

A further aspect of the invention provides a method and server system for processing patient test data from a plurality of point of care device types in which patient test data is received from a point of care computer using a point of care interface, the point of care computer receiving the patient test data from a plurality of point of care device types and passing it unchanged, the plurality of point of care device types having different data formats; a library of test type objects is stored in a library store, each test type object defining a common data structure for a type of patient test; the point of care device is identified from the patient test data to select a parser module specific for the point of care device; the patient test data is parsed using the selected parser module to identify a test type; and the parsed data is processed using the library of test type objects to store the patient test data as an instance of the identified test type.

This aspect of the invention enables patient test data for different point of care devices outputting data in different formats to be translated or parsed into and stored in a data format, which is common for common patient test types e.g. urinalysis.

DETAILED DESCRIPTION OF EMBODIMENTS OF THE INVENTION

Figure 1:
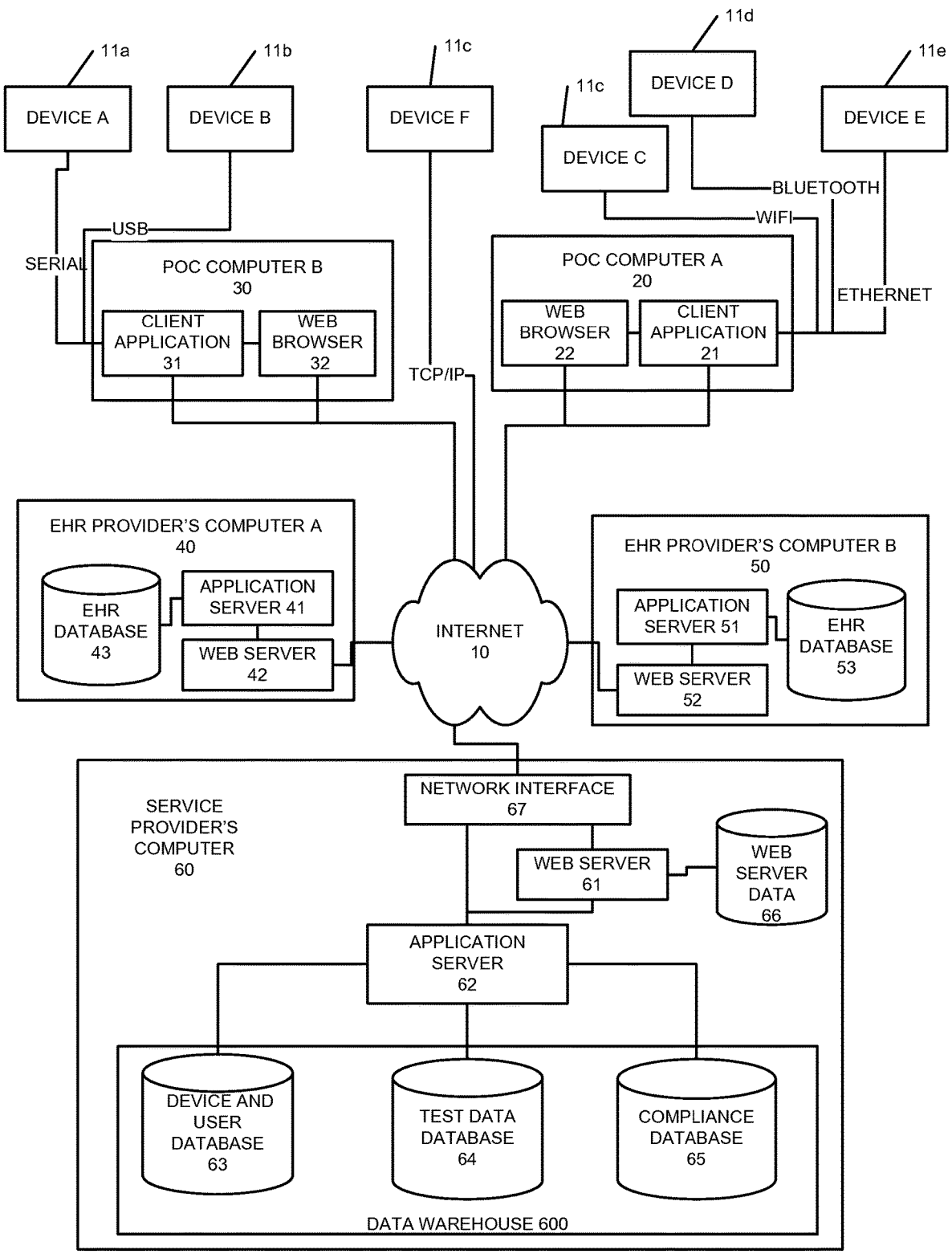
FIG. 1 is a schematic diagram of a system for processing patient test data according to one embodiment of the invention.

A first generalised embodiment comprises a point of care computer comprising a device interface for receiving patient test data for a patient test from a point of care device; a network interface for transmitting the patient test data to a remote server system; program memory for storing a software application; a processor for reading and implementing the software application in the memory; and an operator interface to allow an operator to input data; wherein the program memory stores an application for implementation by the processor to control the device interface to receive the patient test data, to control the network interface to transmit the patient test data to the server and to receive data identifying additional required data, to control the operator interface to generate a display interface indicating the additional required data and to receive operator input data in response, and to control the network interface to transmit the operator input data to the server system.

In one embodiment the application is adapted to be implemented by the processor to add point of care computer identifier data and device identifier data to the test data for transmission by the network interface to the server system.

In one embodiment the application is adapted to be implemented by the processor to determine the device identifier data dependent upon parameters for the device interface.

In one embodiment the application is adapted to be implemented by the processor to control the operator interface to receive operator identification information for transmission by the network interface for the association of operator identifier data with the patient test data.

In one embodiment the application is adapted to be implemented by the processor to cause the operator interface to check the received operator input data for input errors.

In one embodiment the application is adapted to be implemented by the processor to control the network interface to receive complete patient test data comprising the patient test data and the operator input data, and to cause the operator interface to display the complete patient test data and to receive an operator response input.

A second generalised embodiment comprises a server system for processing patient test data from at least one point of care device, the server system comprising a point of care interface for receiving patient test data from a point of care computer, the point of care computer receiving the patient test data from at least one point of care device; program memory for storing software; and a processor for reading and implementing the software in the memory; wherein the program memory stores software for implementation by the processor to control the point of care interface to receive the patient test data from the point of care computer, to identify additional required data missing from the patient test data according to electronic health record provider requirements, to control the point of care interface to indicate to the point of care computer the additional required data to be input by an operator of the point of care computer and to receive operator input data, and to add the operator input data to the patient test data to form complete patient test data.

In one embodiment the server system includes an electronic health record interface for sending and receiving data to and from electronic health record providers; wherein the software is adapted to be implemented by the processor to control the electronic health record interface to obtain the electronic health recorder provider requirements.

In one embodiment the software is adapted to be implemented by the processor to control the electronic health record interface to transmit the complete patient test data to the electronic health record provider.

In one embodiment the software is adapted to be implemented by the processor to convert the received patient test data to a structure common to patient test data from a plurality of point of care devices.

In one embodiment the software is adapted to be implemented by the processor to convert the received patient test data in the structure common to patient test data from a plurality of point of care devices into a structure specific to one of a plurality of electronic health record providers.

In one embodiment the software is adapted to be implemented by the processor to control the point of care interface to receive operator information, and to derive and associate operator identifier data with the patient test data.

In one embodiment the server system includes a cache memory for storing the patient test data until the complete patient test data is formed.

In one embodiment the software is adapted to be implemented by the processor to check the received patient test data and operator input data for errors.

In one embodiment the software is adapted to be implemented by the processor to control the point of care interface to transmit the complete patient test data to the point of care computer for display to the operator, and to receive an operator response input.

A third generalised embodiment comprises a method of operating a point of care computer, the method comprising receiving patient test data for a patient test from a point of care device over a device interface; transmitting the patient test data to a remote server system over a network; receiving data identifying additional required data; generating a display interface on a display indicating the additional required data; receiving operator input data in response from a user input device; and transmitting the operator input data to the server system over the network.

In one embodiment the method includes adding point of care computer identifier data and device identifier data to the test data for transmission to the server system.

In one embodiment the method includes determining the device identifier data dependent upon parameters for the device interface.

In one embodiment the method includes receiving operator identification information from the user input device for transmission by the network interface for the association of operator identifier data with the patient test data.

In one embodiment the method includes checking the received operator input data for input errors.

In one embodiment the method includes receiving complete patient test data over the network comprising the patient test data and the operator input data, displaying on the display the complete patient test data, and receiving an operator response input from the user input device.

A fourth generalised embodiment comprises a method of operating a server system to process patient test data from at least one point of care device, the method comprising receiving patient test data from a point of care computer from a point of care interface, the point of care computer receiving the patient test data from at least one point of care device; identifying additional required data missing from the patient test data according to electronic health record provider requirements; using the point of care interface to transmit an indication to the point of care computer of the additional required data to be input by an operator of the point of care computer; receiving operator input data from the point of care computer; and adding the operator input data to the patient test data to form and store complete patient test data.

In one embodiment the method includes controlling an electronic health record interface to obtain the electronic health recorder provider requirements from an electronic heath record provider over a network.

In one embodiment the method includes transmitting the complete patient test data to the electronic health record provider.

In one embodiment the method includes converting the received patient test data to a structure common to patient test data from a plurality of point of care devices.

In one embodiment the method includes converting the received patient test data in the structure common to patient test data from a plurality of point of care devices into a structure specific to one of a plurality of electronic health record providers.

In one embodiment the method includes receiving operator information over the point of care interface, and deriving and associating operator identifier data with the patient test data.

In one embodiment the method includes storing the patient test data in a cache memory until the complete patient test data is formed.

In one embodiment the method includes checking the received patient test data and operator input data for errors.

In one embodiment the method, includes transmitting the complete patient test data to the point of care computer for display to the operator, and receiving an operator response input.

A fifth generalised embodiment comprises a computer system for determining regulatory compliance for point of care patient testing by operators using point of care devices, the computer system comprising an operator data store storing operator data for a plurality of point of care device operators, the operator data including information for each operator indicating qualifications for the point of care devices and/or types of patient tests; a device data store storing point of care device data for a plurality of point of care devices, the point of care device data including records of quality control tests and/or maintenance data for each point of care device; a regulatory compliance data store storing regulatory compliance requirement data on requirements for medical patient testing regulatory compliance; an interface for receiving patient test data and data identifying the operator and the point of care device; a patient test data store for storing the received patient test data; and a processor for processing the stored data using the stored operator data, point of care device data, and regulatory compliance requirement data to determine if the patient test is regulatory compliant, and for indicating in the patient test data store whether or not the patient test data is regulatory compliant.

In one embodiment the computer system includes a network interface for interfacing to at least one remote electronic health record computer, wherein the processor is adapted to transmit patient test data that is regulatory compliant to the at least one remote electronic health record computer.

In one embodiment the processor is adapted to transmit patient test data that is not regulatory compliant with data indicating that the patient test data that is not regulatory compliant to the at least one remote electronic health record computer, so that the at least one remote electronic health record computer stores the patient test data that is not regulatory compliant marked accordingly.

In one embodiment the processor is adapted to prevent the transmission of patient test data that is not regulatory compliant to the at least one remote electronic health record computer.

In one embodiment the computer system includes an operator data interface for entry of the information for each operator indicating qualifications for the point of care devices and/or types of patient tests.

In one embodiment the computer system includes a device data interface for entry of quality control test data for each point of care device for storage in the data device store as the records of quality control tests for each point of care device.

In one embodiment the maintenance data includes point of care device calibration data indicative of the calibration history for the at least one point of care device.

A sixth generalised embodiment comprises a computer implemented method of determining regulatory compliance for point of care patient testing by operators using point of care devices, the method system comprising storing operator data for a plurality of point of care device operators in an operator data store, the operator data including information for each operator indicating qualifications for the point of care devices and/or types of patient tests; storing point of care device data for a plurality of point of care devices in a device data store, the point of care device data including records of quality control tests and/or maintenance data for each point of care device; storing regulatory compliance requirement data on requirements for medical patient testing regulatory compliance in a regulatory compliance data store; receiving patient test data and data identifying the operator and the point of care device at a computer interface; storing the received patient test data in a patient test data store; and using a processor to process the stored data using the stored operator data, point of care device data, and regulatory compliance requirement data to determine if the patient test is regulatory compliant, and to indicate in the patient test data store whether or not the patient test data is regulatory compliant.

In one embodiment the computer implemented method includes transmitting patient test data that is regulatory compliant to the at least one remote electronic health record computer.

In one embodiment the computer implemented method includes transmitting patient test data that is not regulatory compliant with data indicating that the patient test data that is not regulatory compliant to the at least one remote electronic health record computer, so that the at least one remote electronic health record computer stores the patient test data that is not regulatory compliant marked accordingly.

In one embodiment the computer implemented method includes preventing the transmission of patient test data that is not regulatory compliant to the at least one remote electronic health record computer.

In one embodiment the computer implemented method includes providing an operator data interface for entry of the information for each operator indicating qualifications for the point of care devices and/or types of patient tests.

In one embodiment the computer implemented method includes providing a device data interface for entry of quality control test data for each point of care device for storage in the data device store as the records of quality control tests for each point of care device.

In one embodiment the maintenance data includes point of care device calibration data indicative of the calibration history for the at least one point of care device.

A seventh generalised embodiment comprises a server system for processing patient test data from a plurality of point of care device types, the server system comprising a point of care interface for receiving patient test data from a point of care computer, the point of care computer receiving the patient test data from a plurality of point of care device types and passing it unchanged, the plurality of point of care device types having different data formats; a library store storing a library of test type objects, each test type object defining a common data structure for a type of patient test; program memory for storing software; and a processor for reading and implementing the software in the memory; wherein the program memory stores software for implementation by the processor to control the point of care interface to receive the patient test data from the at least one point of care computer, to identify the point of care device from the patient test data to select a parser module specific for the point of care device, to parse the patient test data using the selected parser module to identify a test type, and to process the parsed data using the library of test type objects to store the patient test data as an instance of the identified test type.

In one embodiment the server system includes a network interface for transmission of the patient test data to one of a plurality of electronic health record providers' computers, wherein the software is adapted to be implemented by the processor to identify the electronic health record providers' computer to which the patient test data is to be transmitted, to select an interface module for the identified electronic health record providers' computer, to implement the selected interface module to convert the format of the patient test data to a format specific to the electronic health record providers' computer, and to control the network interface to transmit the converted patient test data to the electronic health record providers' computer.

An eighth generalised embodiment comprises a computer implemented method of processing patient test data from a plurality of point of care device types, the method comprising receiving patient test data from a point of care computer using a point of care interface, the point of care computer receiving the patient test data from a plurality of point of care device types and passing it unchanged, the plurality of point of care device types having different data formats; storing a library of test type objects in a library store, each test type object defining a common data structure for a type of patient test; identifying the point of care device from the patient test data to select a parser module specific for the point of care device; parsing the patient test data using the selected parser module to identify a test type; and processing the parsed data using the library of test type objects to store the patient test data as an instance of the identified test type.

In one embodiment the computer implemented method includes identifying an electronic health record providers' computer to which the patient test data is to be transmitted using a network interface; selecting an interface module for the identified electronic health record providers' computer; implementing the selected interface module to convert the format of the patient test data to a format specific to the electronic health record providers' computer; and transmitting the converted patient test data to the electronic health record providers' computer using the network interface.

In one embodiment a non-transient storage medium stores computer readable code for controlling a computer to carry out any of the methods as described above.

In one embodiment a carrier medium carries computer readable code for controlling a computer to carry out any of the methods as described above.

In the following detailed description, reference is made to the accompanying drawings that form a part hereof, and in which is shown by way of illustration specific embodiments in which the inventive subject matter may be practiced. These embodiments are described in sufficient detail to enable those skilled in the art to practice them, and it is to be understood that other embodiments may be utilized and that structural, logical, and electrical changes may be made without departing from the scope of the inventive subject matter. Such embodiments of the inventive subject matter may be referred to, individually and/or collectively, herein by the term "invention" merely for convenience and without intending to voluntarily limit the scope of this application to any single invention or inventive concept if more than one is in fact disclosed.

The following description is, therefore, not to be taken in a limited sense, and the scope of the inventive subject matter is defined by the appended claims.

The functions or algorithms described herein are implemented in hardware, software or a combination of software and hardware in one embodiment. The software comprises computer executable instructions stored on computer readable media such as memory or other type of storage devices, or any other form of media such as a signal. Further, described functions may correspond to modules, which may be software, hardware, firmware, or any combination thereof. Multiple functions are performed in one or more modules as desired, and the embodiments described are merely examples. The software is executed on a digital signal processor, ASIC, microprocessor, or other type of processor operating on a system, such as a personal computer, server, a mobile device, or other device capable of processing data including network interconnection devices. The network can comprise a wired or wireless network and includes a private network, a virtual private network (VPN), a Local Area Network (LAN), a Wide Area Network (WAN) and the internet for example. Although in the following detailed embodiment the interconnection between computers is shown over the internet, the invention encompasses any form of network connection.

Some embodiments implement the functions in two or more specific interconnected hardware or software modules or devices with related control and data signals communicated between and through the modules, or as portions of an application-specific integrated circuit. Thus, the exemplary process flow is applicable to software, firmware, and hardware implementations.

Embodiments of the present invention can be implemented on any form of computing hardware using one or more computer programs or applications (software). The computer program(s) can be provided to a computer on any suitable carrier medium. One such type of medium is a computer storage medium which represents a non-transient medium. Computer storage media include random access memory (RAM), read only memory (ROM), erasable programmable read-only memory (EPROM) and electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions. Another form of medium is a transient medium such as a signal. A signal can comprise an electrical signal over a wire, an electromagnetic signal transmitted over a wire or wirelessly, an optical signal, an acoustic signal, or even a magnetic signal. Once common form of signal is transmitted over a communication network which can be wired or wireless or a combination of both, e.g. a local area network (LAN), a wide area network (WAN) or the internet.

The point of care devices can comprises any device for carrying out any patient medical test at a point of care facility or even at the patients premises, such as blood glucose testing, blood gas and electrolytes analysis, rapid coagulation testing, rapid cardiac markers diagnostics, drugs of abuse screening, urine strips testing, pregnancy testing, faecal occult blood analysis, food pathogens screening, haemoglobin diagnostics, infectious disease testing and cholesterol screening. A point of care facility can comprise any medical facility capable of providing such patient tests such as a doctor's surgery, a clinic, or a specialist centre. Where a point of care device is used by a patient in their own facilities either by themselves or by a visiting medical practitioner, the patient test data can be obtained as an output from the device on a storage media for later upload to a point of care computer, or as a signal to be transmitted over a communications network (wired or wireless) to the point of care computer).

A first embodiment of the present invention will now be described with reference to FIG. 1.

FIG. 1 schematically illustrates a patient test data gathering and processing system. Point of care devices 11a to 11d are provided to obtain patient test data. The point of care devices 11a to 11f are connected to interfaces in respective point of care (POC) computers 20 and 20. The POC computers 20 and 30 are provided at POC facilities or accessible to POC facilities. The POC devices 11a to 11f may be present at the POC facility or used at a remote location when portable e.g. at the patients premises or in a mobile facility. The POC devices 11a to 11f generate output patient test data as a result of a test being performed by an operator on a patient. The patient test data can be output using any known convenient method which depends upon the output capabilities of the POC device and includes:

From POC device A (11a) over a serial computer line to a serial computer port in the POC computer 30

From POC device B (11b) over a USB link to a USB computer port in the POC computer 30

From POC device C (11c) over a wireless Wi-Fi link to a wireless port in the POC computer 20

From POC device D (11d) over a Bluetooth® link to a Bluetooth® port in the POC computer 20

From POC device E (11e) over an Ethernet line to an Ethernet port in the POC computer 20

From POC device F (11f) over an internet connection to a an internet network interface the POC computer 20

From a POC device the patient test data can also be stored onto a storage device such as a solid state memory device, an optical disk or even a magnetic disk to be read by an appropriate storage device in the POC computer.

The POC computer 20 and 30 comprises any suitable computing device such as a general purpose computer, a mobile device, a laptop, tablet computer etc. The POC computer 20 and 30 implements computer code in the form of a web browser application 22 and 32 and a client application 21 and 31. The POC computer 20 and 30 has a connection via a network interface to the internet 10 over a wired or wireless network to provide the web browser application 22 and 33 and the client application 21 and 31 with access to send and receive data over the internet 10.

Electronic health records (EHR) are stored and maintained by EHR providers. There are a number of such providers available and different medical care providers use different EHR providers. The EHR providers host the HER records in databases 43 and 53 on computers 40 and 50. Each EHR provider's computer 40 and 50 implements a web server 42 and 52 for interfacing via a network interface to the internet 10 and an application server 41 and 51 for providing the required functionality and interface to the respective EHR databases 43 and 53.

In this embodiment, the patient test data processing is hosted in a service provider's computer 60 comprising a server system implementing a Software as a Service model, where a 'thin client' in the form of the client application 21 and 31 is implemented on each POC computer 20 and 30. On the service provider's computer 60 web services are implemented to provide the functionality. On the POC computer 30 and 30 a Windows® service is implemented to provide the functionality.

As shown in FIG. 1 schematically, a web server 61 is provided with access to web server data 66 to provide a web interface to the POC computers 20 and 30. This enables an operator to login into the service and interact with interfaces generated by the web server 61 e.g. to view lists of and select cached patient test data, to input required additional patient test data, to access and input operator qualification data etc. An application server 62 is provided to provide the functionality and access the device and user database 63, the test data database 64 and the compliance database in the data warehouse 600. Both the application server 62 and the web server 61 are connected by a network interface 67 to the internet 10. The device and user interface stores a library of test type objects defining a common data format for a type of test and hence forms a library store.

In the embodiment illustrated in FIG. 1, the system operates such that the operators of the POC devices 11*a* to 11*f* and the POC computers 20 and 30 require access to the EHR records hosted by the EHR provider's computers 40 and 50 i.e. the POC facility does not have its own proprietary EHR and instead access EHR providers available to many POC facilities and providers.

Figure 2:
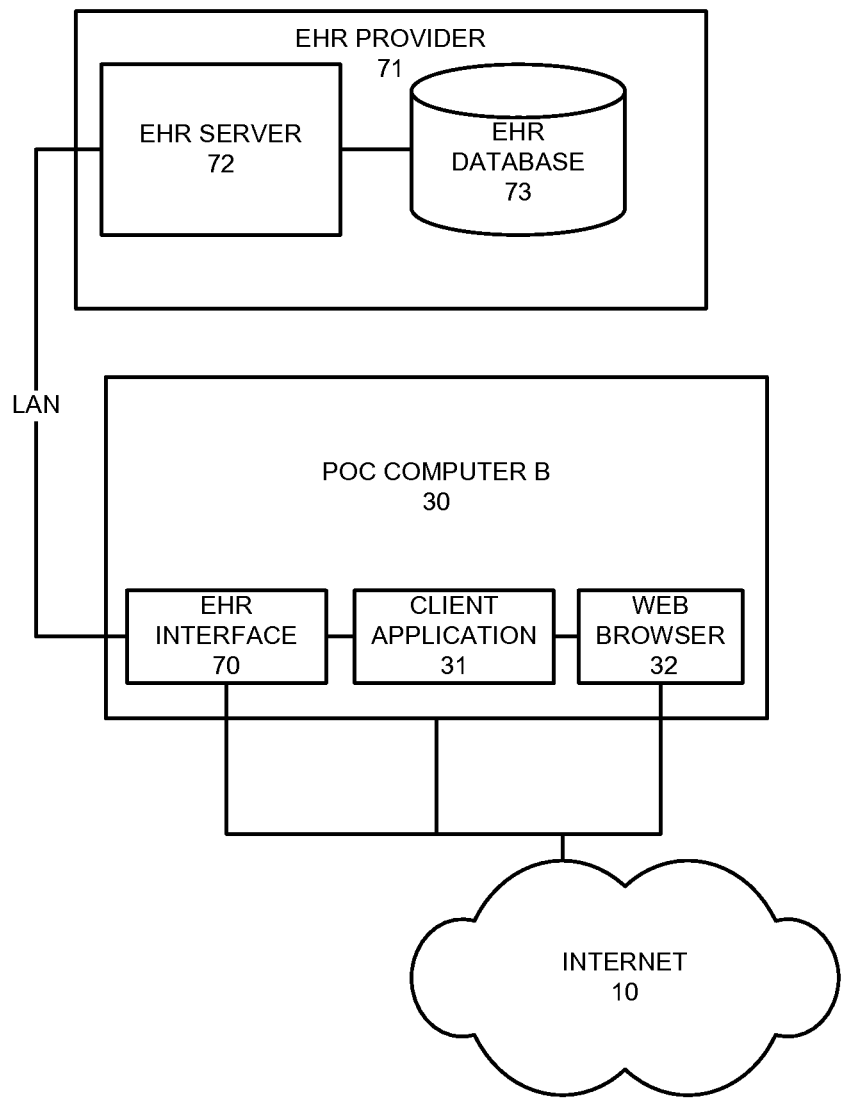
FIG. 2 is a schematic diagram of a modified system of FIG. 1.

The embodiment of FIG. 2 illustrates a modification of the embodiment of FIG. 1 to encompass POC providers and facilities which have their own EHR provider 71 and a direct network connection to that EHR provider 71. In this embodiment, the POC computer 30 is modified to include an EHR interface 70. The EHR interface 70 has a network connection to the EHR provider 71. In this embodiment the network connection is a LAN but could of course be a WAN, a VPN or even a connection over the proprietary connection over the internet. The EHR provider 71 comprises an EHR server 72 providing access to an EHR database 73. In this embodiment, a single POC provider or a group may have direct access from their POC computers to their own EHR provider 71. This embodiment operates in a manner similar to the first embodiment as will be described herein after, except that communications to and from the service provider's computer 60 can either go directly to the EHR provider 71 if a direct internet connection is provided or via the EHR interface 70 in the POC computer 20 and 30.

Figure 3:
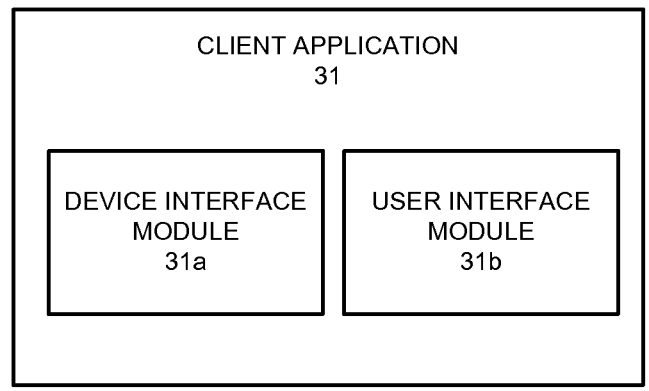
FIG. 3 is a schematic diagram of a client application according to one embodiment of the present invention.

FIG. 3 is a schematic diagram of a client application according to one embodiment. The client application 31 comprises two distinct functional modules, namely a device interface module 31*a* for sending and receiving data to and from POC devices 11*a* to 11*f*, and a user interface module 31*b* for interfacing with the service provider's computer 60 to generate a user interface to allow a user to interact with the service. The user interface module 31*b* can interact with the web browser application 32 to provide a web interface to enable an operator to login, to view a list of and select cached patient test data, to enter required additional patient test data, to enter and view operator qualification data for regulatory compliance etc. In this embodiment, the device interface module 31*a* is responsible for receiving and passing on the patient test data output from the POC device 11*a* to 11*f*, and the user interface module 31*b* is responsible for identifying to an operator the required additional data to enable the operator to input the required additional data for transmission by the user interface module 31*b* to the service provider's computer 60.

Figure 4:
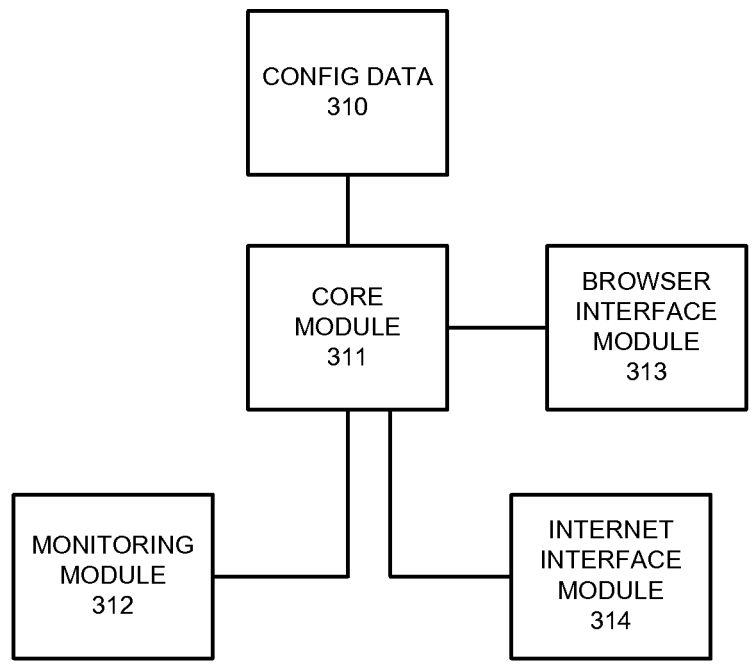
FIG. 4 is a schematic diagram of a client application according to one embodiment of the present invention.

FIG. 4 is a different schematic diagram of a client application 31 according to an embodiment of the invention. This schematic diagram illustrates that the client application 31 is composed of functional modules comprising configuration data 310 stored in non-volatile memory in the POC computer 30 storing configuration parameters for each POC device 11*a* to 11*f* connected to the POC computer 30. The configuration parameters can be entered by an operator, automatically detected, or downloaded from the service provider's computer 60 as will be described in more detail herein after. A monitoring module 312 monitors the network and input ports of the POC computer 30 for data output to the POC computer 30 by the POC device 11*a* to 11*f*. A core module 311 controls the monitoring module 312 in according with the configuration parameters and receives the input patient test data and adds the POC device identifier and POC computer identifier to it before passing it to an internet interface module 314 to transmission to the service provider's computer 60. A browser interface module 313 is provided and controlled by the core module 311 to cause the web browser 32 to launch a browser window to receive generate an operator login interface to enable an operator to login to the service after having performed a test to select and approve the test, whereby the web browser 32 receives a web page for entry for required additional data to complete a patient test record.

Figure 5:
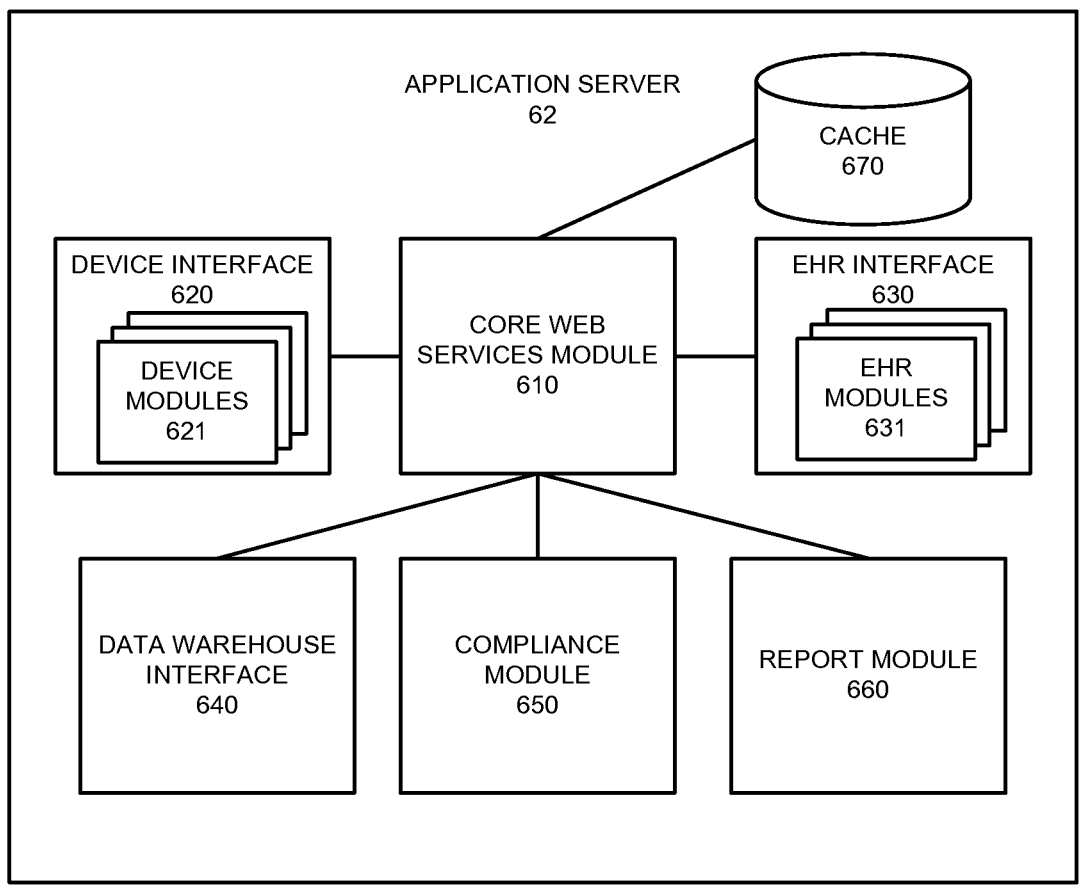
FIG. 5 is a schematic diagram of an application server according to one embodiment of the invention.

FIG. 5 is a schematic diagram of an application server 62 hosted on the service provider's computer system according to one embodiment. The application server 62 operates a core web services module 610 which has access to a cache memory 670 for temporary storage of patient test data pending approval and completion by operators, and which provides an interface 640 to the data warehouse 600. A compliance module 650 is implemented to provide regulatory compliance functionality as will be described herein after. A reports module 660 is provided to enable users of the service with access to reports on patient tests and compliance. A device interface module 620 is provided which implements specific device modules 621 dependent upon the identity of the devices detected in the patient test data. The device modules 621 receive the patient test data and perform device specific processing on it, namely the data which is in a format specific to the device is parsed using a parser specific to the device to reformat the data according to a test type object dependent upon the test type identified for the patient test data. The library of test type objects in the data warehouse 600 is accessed to identify the test type. The patient test data reformatted according to the identified test type can then be stored in the cache 670 pending approval and completion by the operator. An EHR interface 630 is also provided and implements EHR modules 631 which are specific to the EHR provider to which the patient test data is to be transmitted. The EHR provider can be identified from an order identifier associated with the patient test. When a medical practitioner places an order for a POCT in an EHR, the order is assigned a unique identifier and it is associated with the patient record and patient identifier in the EHR. As will be described in more detail herein after, when a patient test is performed an operator will input a patient name or identifier enabling the order to be found in the EHR and hence associated with the patient test data in the cache 670 of the service provider's computer 60 pending completion and acceptance of the patient test data by the operator.

Figure 6A:
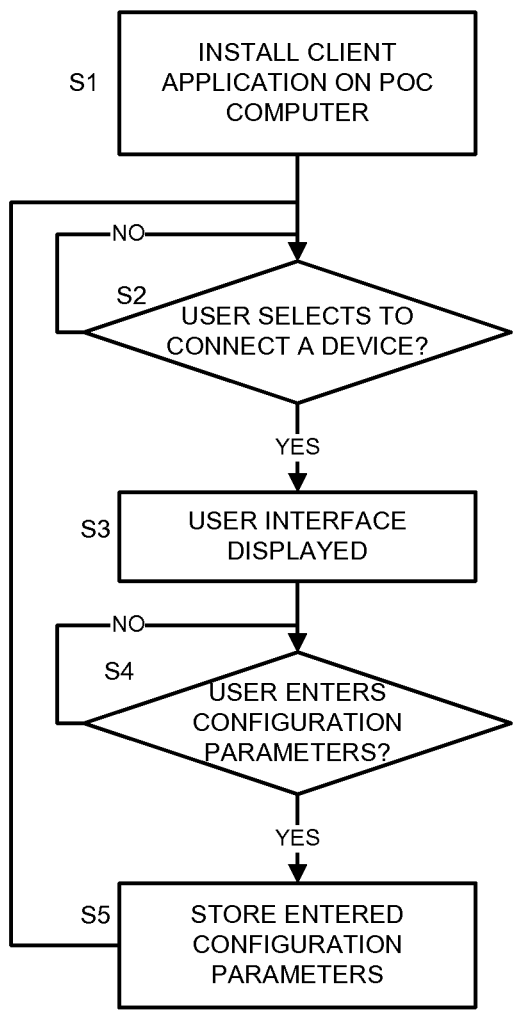
FIGS. 6a to 6c are flow diagrams illustrating alternative methods of installing and configuring the client application according to one embodiment of the invention.
Figure 6B:
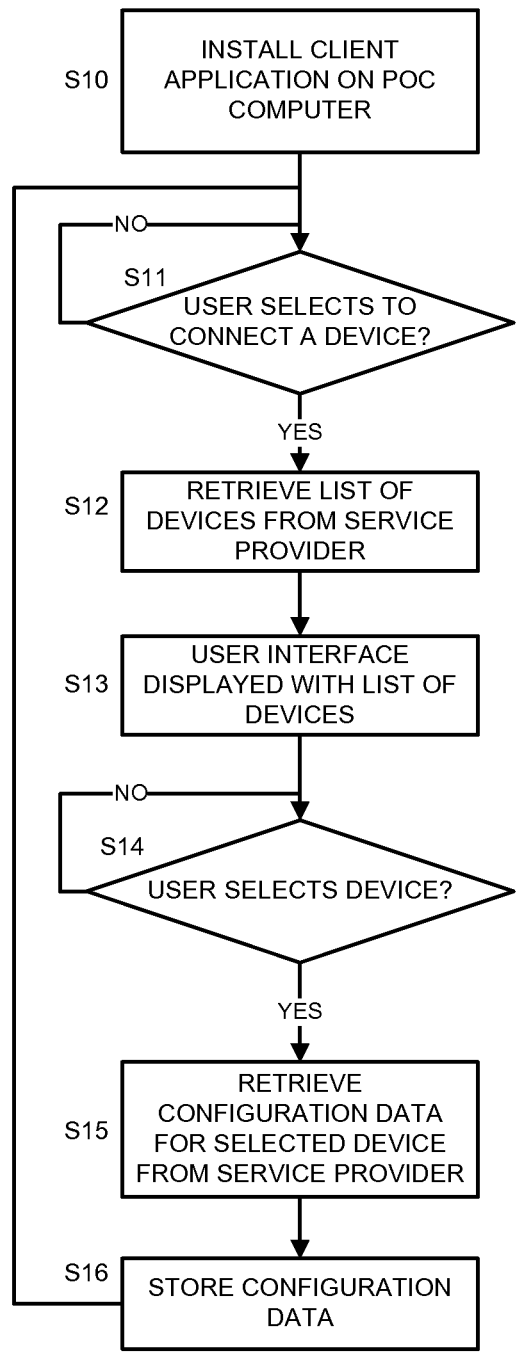
Figure 6C:
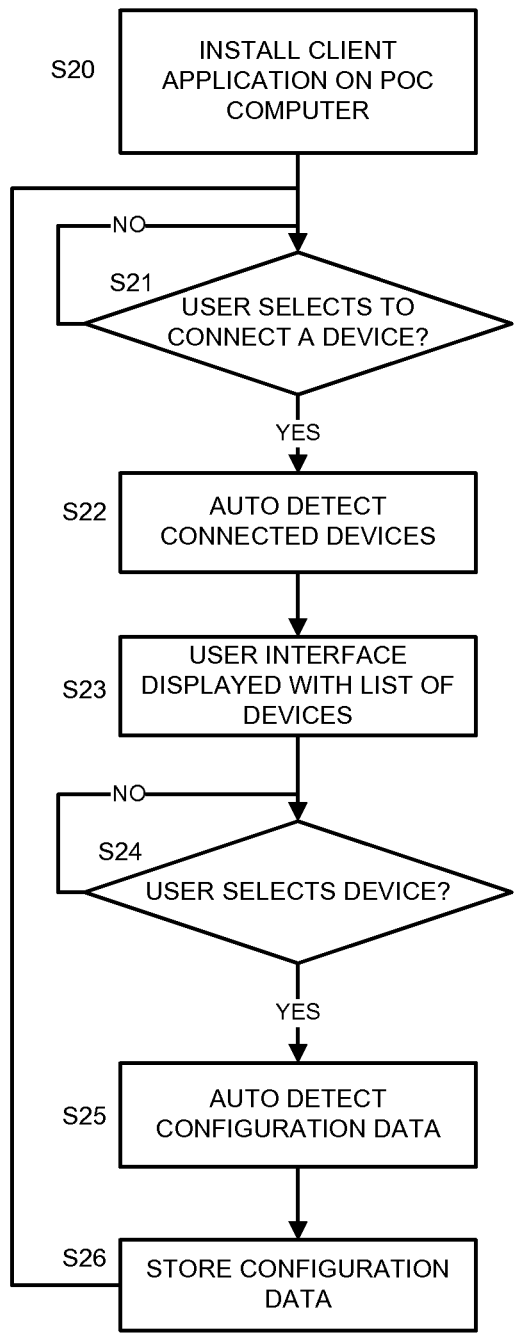

FIGS. 6*a* to 6*c* are flow diagrams illustrating different methods of configuring the client application 21 and 31 on the POC computer 20 and 30. The intention is to provide a thin client application that is common to all devices and can be easily configured for different POC devices.

Referring now to FIG. 6a, in step S1 the operator of the POC computer 20 and 30 downloads and installs the client application code onto the POC computer 20 and 30. When a user selects to connect a new POC device 11a to 11f (step S2) a user interface is displayed (step S3) and the operator is prompted to enter configuration parameters. Such parameters include a device name, a connection type e.g. USB, Wi-Fi_33, serial, Ethernet, or Bluetooth, connection parameters e.g. port number, baud rate, parity etc. In addition to the POC device name, each POC device is assigned a unique identifier since a POC computer may be connected with more than one POC device with the same name e.g. ABC Inc Blood Tester. These entered configuration parameters are then stored with a device identifier (or the device name) (step S5). This process is simple and enables common code to be used for all devices. Once the configuration parameters are entered by the operator, the client application 21 and 31 will monitor for inputs from the POC device e.g. the configuration data could specify to monitor for input data on serial port COM 1 for device A 11a configured to input on serial port COM 1, or to monitor over TCP/IP port 9000 for device E 11e.

Referring now to FIG. 6b, in step S10 the operator of the POC computer 20 and 30 downloads and installs the client application code onto the POC computer 20 and 30. When a user selects to connect a new POC device 11a to 11f (step S11) a list of POC devices supported by the service is retrieved from the service provider's computer 60 (step S12) and a user interface is displayed listing the available POC devices for configuration for the service (step S13). A user then selects the appropriate POC device for installation from the displayed list (step S14) and configuration data parameters for the selected POC device is then retrieved from the service provider's computer 60. Such parameters include a device identifier and name, a connection type e.g. USB, Wi-Fi, serial, Ethernet, or Bluetooth, connection parameters e.g. port number, baud rate, parity etc. In addition to the POC device name, each POC device is assigned a unique identifier since a POC computer may be connected with more than one POC device with the same name e.g. ABC Inc Blood Tester. These retrieved configuration parameters are then stored (step S16). This process avoids the need for the operator to have to input the configuration parameters and instead relies on having a library of configuration parameters for POC devices stored in the service provider's computer 60.

Referring now to FIG. 6c, in step S20 the operator of the POC computer 20 and 30 downloads and installs the client application code onto the POC computer 20 and 30. When a user selects to connect a new POC device 11a to 11f (step S21) the client application performs an auto detection routine to detect the identity of the connected POC devices. Such a routine could require the POC device to send a set of trial test data for example. A user interface is then displayed listing the connected POC devices (step S23 and the user can select to enable any of the connected POC devices (step S24). The client application then carried out an auto detection routine to detect configuration data parameters for the selected POC devices (step S25). Such parameters include a device name, a connection type e.g. USB, Wi-Fi_33, serial, Ethernet, or Bluetooth, connection parameters e.g. port number, baud rate, parity etc. In addition to the POC device name, each POC device is assigned a unique identifier since a POC computer may be connected with more than one POC device with the same name e.g. ABC Inc Blood Tester. These determined configuration parameters are then stored (step S26). This process is avoids the need for any input by the operator or the need for a library of configuration data for the POC devices, but it does require an algorithm for detecting the connection of POC devices and then for determining the configuration data.

In all of the above embodiments, once the client application is installed, an operator may at any time connect a new device and new configuration parameters need to be added accordingly.

A method of operating the patient test processing system according to one embodiment will now be described with reference to FIGS. 7a and 7b.

A patient test is performed on a patient in step S30 and the POC device outputs the patient test data (step S31). The patient test data is received by the POC computer 20 via a POC interface such as a serial interface, a USB interface, an Ethernet interface, a Wi-Fi interface or a Bluetooth® interface and 30 (step S32) and the client application 21 and 31 adds an identifier for the device POC computer 20 and 30, and a unique identifier and name for the POC device to the patient test data. The patient test data is then transmitted over a network interface to the service provider's computer 60. Upon receipt at the service provider's computer 60 the device name is used to identify the device module 621 to implemented to process the patient test data from the POC device. The device module 621 verifies that the data is of the format that was expected for the POC device, parses the patient test data and stores the parsed patient test data in the cache 670 (step S36) and constructs a response to the received patient test data (step S37), which is transmitted to the POC computer and passed to the POC device (steps S38 and S39). Some POC devices send messages before they send the patient test data. The device modules 621 comprise code capable of recognising the messages and sending appropriate responses to their respective POC devices. The parsing performed by the device modules 621 takes the patient test data from the POC device and formats the patient test data according to a test type determined from a test type library on the basis of the POC device name. In other words, each device module 621 is associated with a test type since it is associated with a device type, which can only produce patient test data of a certain test type. More than one device type can be associated with a test type, since different device types could be used to provide a test of the same type e.g. ABC Inc's Blood Monitor is one device type and XYZ's Blood Monitor is another device type but both provide patient test data of the same test type—Blood Test A.

Hence the patient test data in the cache 670 (step S36) comprises incomplete and unverified patient test data which is assigned a unique test identifier.

In step S40, the client application 21 and 31 causes the web browser 22 and 32 to open a user interface in the form of a web page retrieved from the web server 61 of the service provider's computer 60. The web page prompts the operator of the POC computer 20 and 30 (assumed to be the operator of the POC device or at least the medical person responsible for verifying and completing the patient test) to enter operator login parameters. The operator is validated in step S42 in the conventional manner using a database of valid operators on the service provider's computer 60. An operator can use the web page to request a list of all patient tests held in the cache 670 requiring completion and verification from the service provider's computer (step S43). The request will identify the operator by their unique operator identifier. The service provider's computer 60 looks up all patient test data in the cache 670 and returns the test identifier, device name, test type and test date to the POC computer 20 and 30 (step S44). The returned data is displayed at the POC computer enabling the operator to use the web page (user interface) to acknowledge the test that they performed (step S45). In response to the selection by the operator to acknowledge or verify patient test data, the test identifiers for the selected patient tests are sent with the operator identifier to the service provider's computer 60 (step S46) where the operator identifier is associated with the patient test data in the cache 670 (step S47). The web page (user interface) at the POC computer 20 and 30 then displays an input interface allowing the operator to input the patient name or unique identifier or an order identifier (step S48). The input patent name or identifier or order identifier is transmitted via the service provider's computer to the EHR provider's computers 40 and 50 in order look up pending orders matching the patient name or identifier or order identifier (steps S49 and S50). The resultant list of orders, which may be just a list of one, is returned via the service provider's computer 60 to the POC computer 20 and 30 for display as a web page (a user interface) (step S51). The list will include order identifiers which will either inherently include an EHR provider identifier or a separate EHR provider identifier will be provided. The operator then selects an appropriate order that matches the patient test performed (step S52) and this selection is transmitted back to the service provider's computer 60, where the patient test data for the test is stored in the cache 670 with the order identifier and patient identifier (step S53). The application server 62 then identifies fields in the patient test data that are missing for the test type (step S54). The EHR providers set required data fields for patient test data. The application server can obtain this information via the EHR interface 630 and uses this to define required fields in each test type. The required fields in the test type object must include all required fields for all EHR providers for that test type. An HTML form is then generated by the web server 61 in step S55 and transmitted to the POC computer 20 and 30 for display by the web browser 22 and 32 (step S56). The form enables the input or data for the required fields, which can include a field for operator comments or can solely comprise of a field for operator comments. The term required additional data in the context of this invention hence encompasses the provision of comments. However, if the operator decides to add no comments, the requirement for additional data is met by simply returning no comments—the comments data comprises empty data or a null. In this circumstance, the operator has been given the opportunity to comment and has taken the decision that no comments are required. Hence, this effectively comprises information that the operator had no comments to make.

The displayed form can enable an operator to input additional data by free form text, numerals, or by selection of options e.g. by selecting from displayed drop down options. Where the operator can input data, the form can be configured to perform rudimentary known form filling checks e.g. a numeric input can reject non numeric input (step S57). This assists in reducing operator input errors. The user input is then transmitted to the service provider's computer 60, where the data is checked for errors and if no errors are detected the additional data is stored in the cache with the patient test data (step S59). The error checking that can be performed at the service provider's computer is much more sophisticated and can be based on algorithmic rules dependent upon the test type, operator identifier, POC device type etc. The complete patient test data in the cache 670 is then used to generate a patient test data display output in the form of a web page by the web server 61 (step S59) and the web browser 22 and 32 at the POC computer 20 and 30 accesses the web site for display of the complete patient test data (step S60). This enables an operator to select to accept the complete patient test data (step S61), which causes the service provider's computer 60 to send the complete patient test data to the test data database 64 in the data warehouse 600 (step S62). The patient test data is also passed to the EHR interface 630 where the EHR provider to which the patient test data is to be sent is identified from the order identifier and any additional EHR identifier. This identification is used to implement a specific EHR module 631 for the patient test data to be transmitted to the EHR provider. The EHR module 631 has knowledge of the format of the data structure of patient test data in the EHR and can hence parse the patient test data from the test type format common to all patient test data in the service provider's computer 60 to the EHR specific data format or structure. The patient test data is then transmitted to the EHR provider's computer 40 and 50 for storage in the EHR database 43 and 53 associated with the order identifier and the patient identifier.

Figure 8A:
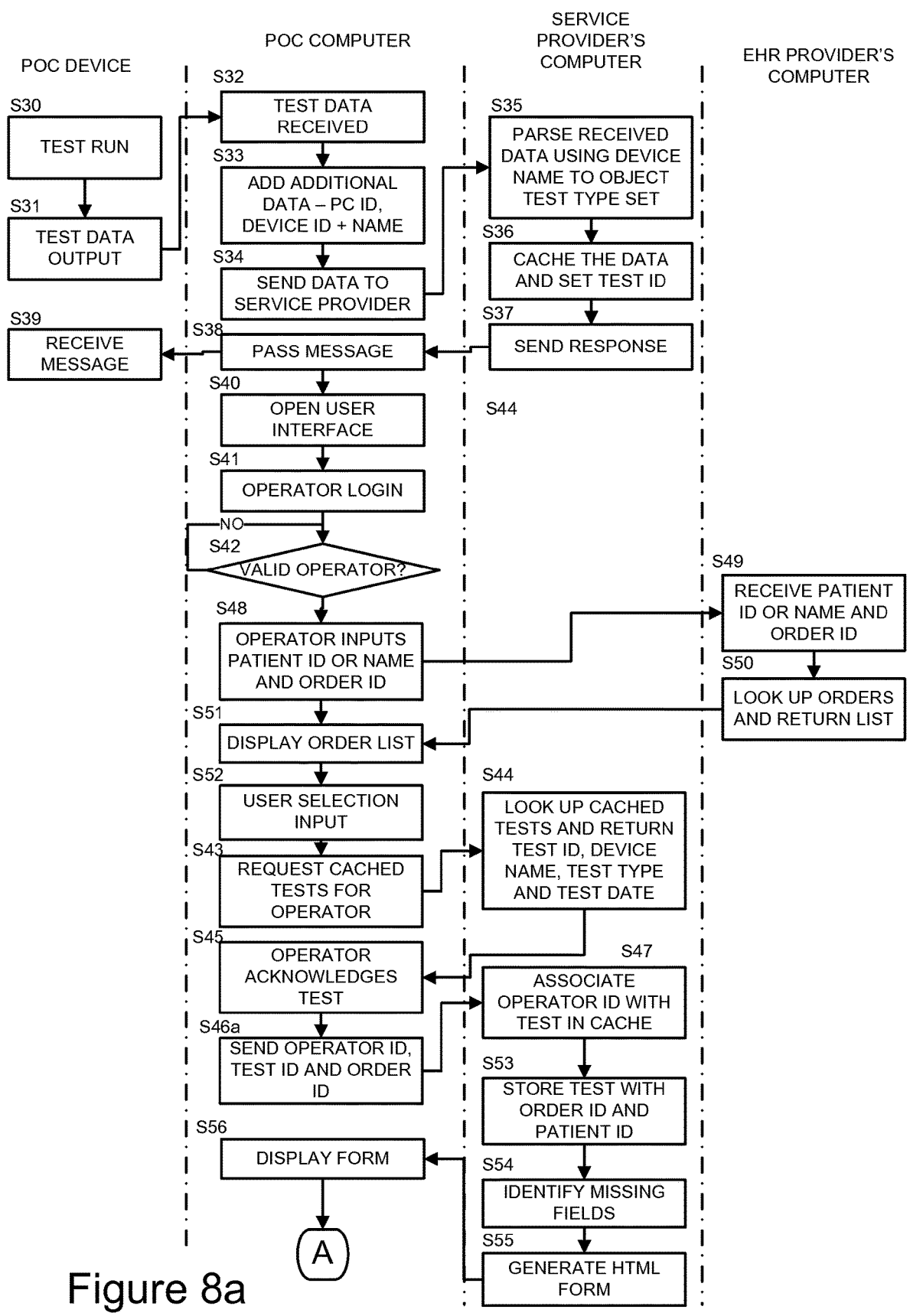
FIGS. 8a and 8b are a flow diagram illustrating the method of processing patient test data according to another embodiment of the invention.
Figure 8B:
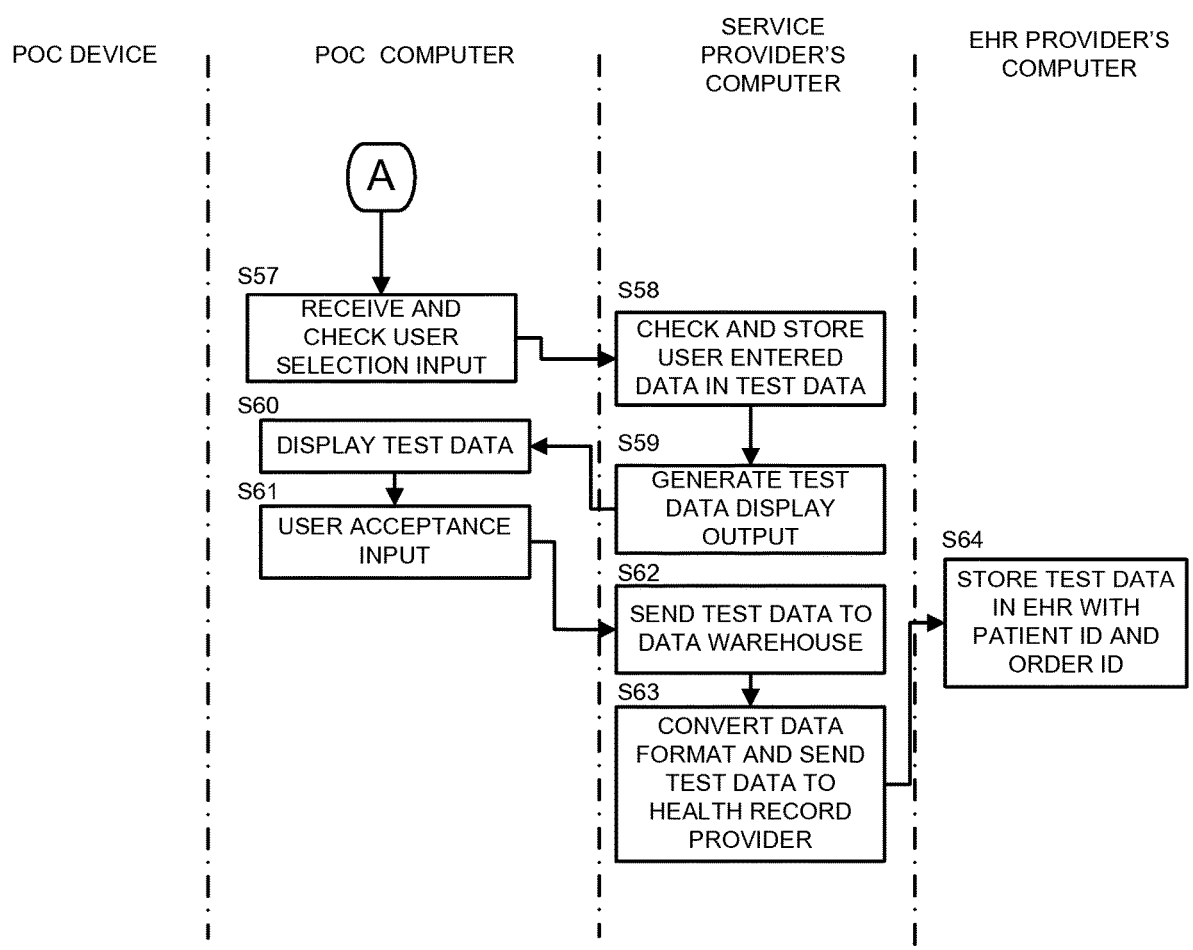

Another method of operating the patient test processing system according to another embodiment will now be described with reference to FIGS. 8*a* and 8*b*. In this embodiment and the previous embodiment, like reference numerals are used for like steps.

A patient test is performed on a patient in step S30 and the POC device outputs the patient test data (step S31). The patient test data is received by the POC computer 20 via a POC interface such as a serial interface, a USB interface, an Ethernet interface, a Wi-Fi interface or a Bluetooth® interface and 30 (step S32) and the client application 21 and 31 adds an identifier for the device POC computer 20 and 30, and a unique identifier and name for the POC device to the patient test data. The patient test data is then transmitted over a network interface to the service provider's computer 60. Upon receipt at the service provider's computer 60 the device name is used to identify the device module 621 to implemented to process the patient test data from the POC device. The device module 621 verifies that the data is of the format that was expected for the POC device, parses the patient test data and stores the parsed patient test data in the cache 670 (step S36) and constructs a response to the received patient test data (step S37), which is transmitted to the POC computer and passed to the POC device (steps S38 and S39). Some POC devices send messages before they send the patient test data. The device modules 621 comprise code capable of recognising the messages and sending appropriate responses to their respective POC devices. The parsing performed by the device modules 621 takes the patient test data from the POC device and formats the patient test data according to a test type determined from a test type library on the basis of the POC device name. In other words, each device module 621 is associated with a test type since it is associated with a device type, which can only produce patient test data of a certain test type. More than one device type can be associated with a test type, since different device types could be used to provide a test of the same type e.g. ABC Inc's Blood Monitor is one device type and XYZ's Blood Monitor is another device type but both provide patient test data of the same test type—Blood Test A.

Hence the patient test data in the cache 670 (step S36) comprises incomplete and unverified patient test data which is assigned a unique test identifier.

In step S40, the client application 21 and 31 causes the web browser 22 and 32 to open a user interface in the form of a web page retrieved from the web server 61 of the service provider's computer 60. The web page prompts the operator of the POC computer 20 and 30 (assumed to be the operator of the POC device or at least the medical person responsible for verifying and completing the patient test) to enter operator login parameters. The operator is validated in step S42 in the conventional manner using a database of valid operators on the service provider's computer 60. The web page (user interface) at the POC computer 20 and 30 then displays an input interface allowing the operator to input the patient name or unique identifier or an order identifier (step S48). The input patent name or identifier or order identifier is transmitted via the service provider's computer to the EHR provider's computers 40 and 50 in order look up pending orders matching the patient name or identifier or order identifier (steps S49 and S50). The resultant list of orders, which may be just a list of one, is returned via the service provider's computer 60 to the POC computer 20 and 30 for display as a web page (a user interface) (step S51). The list will include order identifiers which will either inherently include an EHR provider identifier or a separate EHR provider identifier will be provided. The operator then selects an appropriate order that matches the patient test performed (step S52). An operator can then use the web page to request a list of all patient tests held in the cache 670 requiring completion and verification from the service provider's computer (step S43). The request will identify the operator by their unique operator identifier. The service provider's computer 60 looks up all patient test data in the cache 670 and returns the test identifier, device name, test type and test date to the POC computer 20 and 30 (step S44). The returned data is displayed at the POC computer enabling the operator to use the web page (user interface) to acknowledge the test that they performed (step S45). In response to the selection by the operator to acknowledge or verify patient test data, the test identifiers for the selected patient tests are sent with the operator identifier and the order identifier to the service provider's computer 60 (step S46a) where the operator identifier is associated with the patient test data in the cache 670 (step S47) and the patient test data for the test is stored in the cache 670 with the order identifier and patient identifier (step S53). The application server 62 then identifies fields in the patient test data that are missing for the test type (step S54). The EHR providers set required data fields for patient test data. The application server can obtain this information via the EHR interface 630 and uses this to define required fields in each test type. The required fields in the test type object must include all required fields for all EHR providers for that test type. An HTML form is then generated by the web server 61 in step S55 and transmitted to the POC computer 20 and 30 for display by the web browser 22 and 32 (step S56). The form enables the input or data for the required fields, which can include a field for operator comments or can solely comprise of a field for operator comments. The term required additional data in the context of this invention hence encompasses the provision of comments. However, if the operator decides to add no comments, the requirement for additional data is met by simply returning no comments—the comments data comprises empty data or a null. In this circumstance, the operator has been given the opportunity to comment and has taken the decision that no comments are required. Hence, this effectively comprises information that the operator had no comments to make.

The displayed form can enable an operator to input additional data by free form text, numerals, or by selection of options e.g. by selecting from displayed drop down options. Where the operator can input data, the form can be configured to perform rudimentary known form filling checks e.g. a numeric input can reject non numeric input (step S57). This assists in reducing operator input errors. The user input is then transmitted to the service provider's computer 60, where the data is checked for errors and if no errors are detected the additional data is stored in the cache with the patient test data (step S59). The error checking that can be performed at the service provider's computer is much more sophisticated and can be based on algorithmic rules dependent upon the test type, operator identifier, POC device type etc. The complete patient test data in the cache 670 is then used to generate a patient test data display output in the form of a web page by the web server 61 (step S59) and the web browser 22 and 32 at the POC computer 20 and 30 accesses the web site for display of the complete patient test data (step S60). This enables an operator to select to accept the complete patient test data (step S61), which causes the service provider's computer 60 to send the complete patient test data to the test data database 64 in the data warehouse 600 (step S62). The patient test data is also passed to the EHR interface 630 where the EHR provider to which the patient test data is to be sent is identified from the order identifier and any additional EHR identifier. This identification is used to implement a specific EHR module 631 for the patient test data to be transmitted to the EHR provider. The EHR module 631 has knowledge of the format of the data structure of patient test data in the EHR and can hence parse the patient test data from the test type format common to all patient test data in the service provider's computer 60 to the EHR specific data format or structure. The patient test data is then transmitted to the EHR provider's computer 40 and 50 for storage in the EHR database 43 and 53 associated with the order identifier and the patient identifier.

Figure 9A:
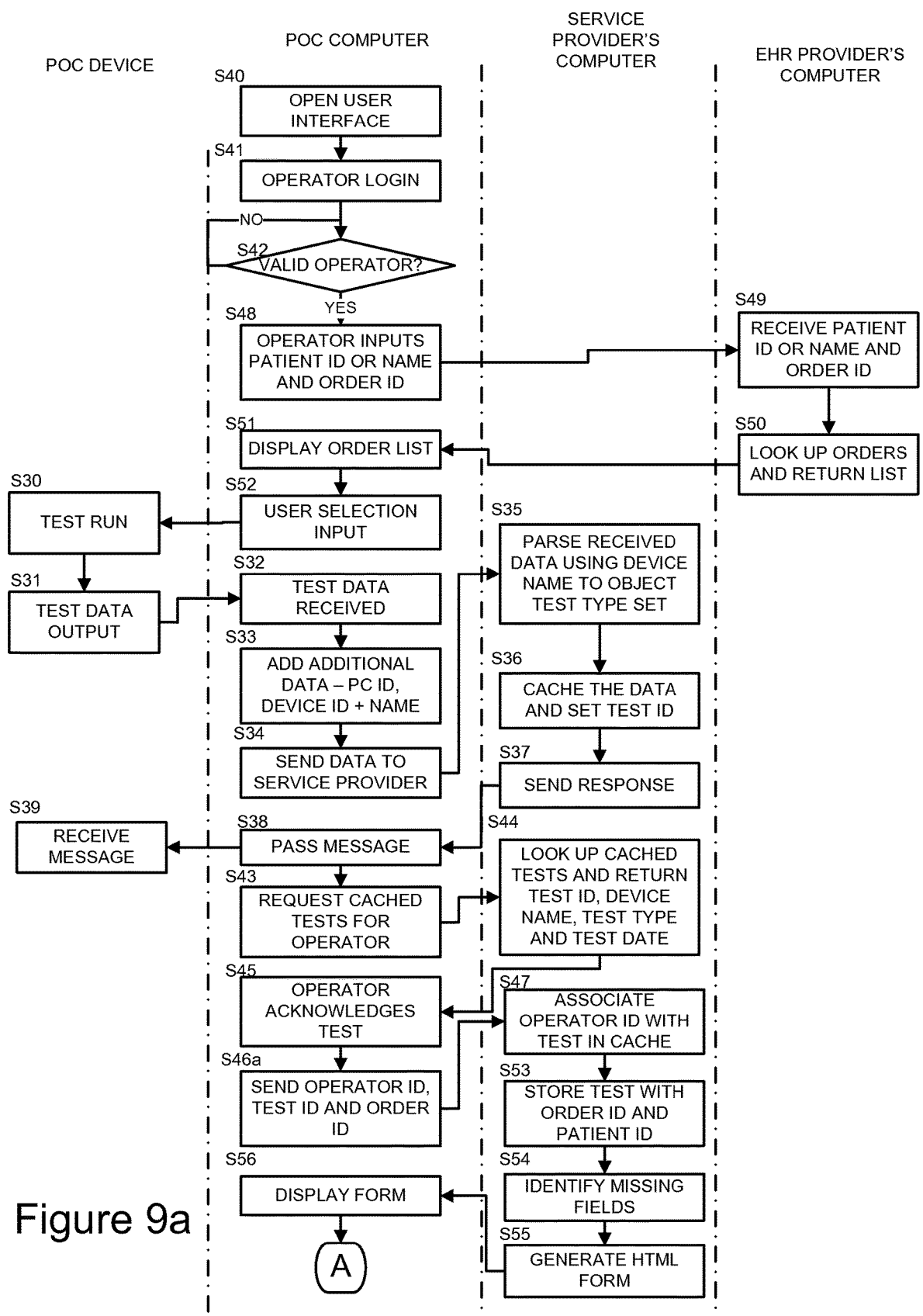
FIGS. 9a and 9b are a flow diagram illustrating the method of processing patient test data according to a further embodiment of the invention.
Figure 9B:
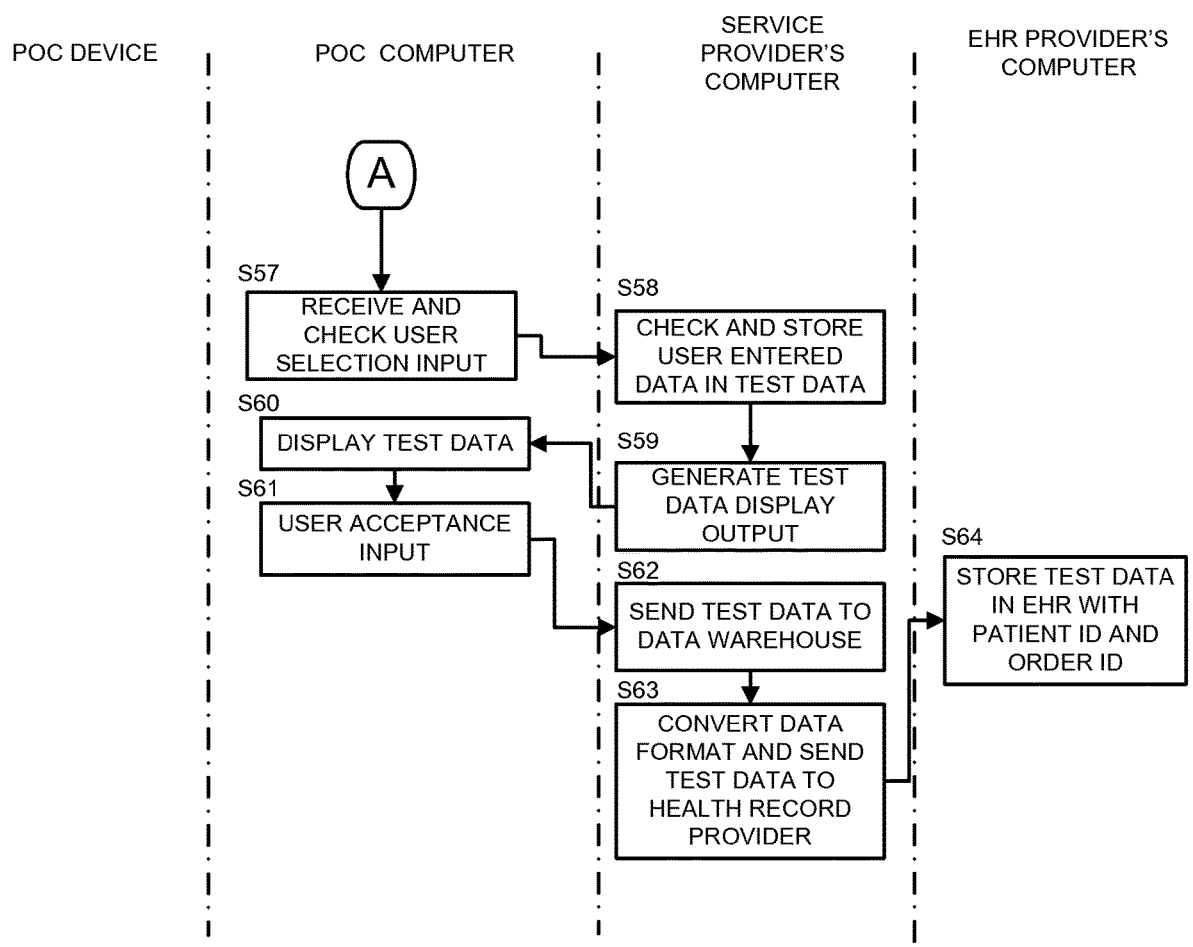

A further method of operating the patient test processing system according to a further embodiment will now be described with reference to FIGS. 9a and 9b. In this embodiment and the previous embodiments, like reference numerals are used for like steps.

In step S40, the client application 21 and 31 causes the web browser 22 and 32 to open a user interface in the form of a web page retrieved from the web server 61 of the service provider's computer 60. The web page prompts the operator of the POC computer 20 and 30 (assumed to be the operator of the POC device or at least the medical person responsible for verifying and completing the patient test) to enter operator login parameters. The operator is validated in step S42 in the conventional manner using a database of valid operators on the service provider's computer 60. The web page (user interface) at the POC computer 20 and 30 then displays an input interface allowing the operator to input the patient name or unique identifier or an order identifier (step S48). The input patent name or identifier or order identifier is transmitted via the service provider's computer to the EHR provider's computers 40 and 50 in order look up pending orders matching the patient name or identifier or order identifier (steps S49 and S50). The resultant list of orders, which may be just a list of one, is returned via the service provider's computer 60 to the POC computer 20 and 30 for display as a web page (a user interface) (step S51). The list will include order identifiers which will either inherently include an EHR provider identifier or a separate EHR provider identifier will be provided. The operator then selects an appropriate order that matches the patient test performed (step S52)

A patient test is then performed on a patient in step S30 and the POC device outputs the patient test data (step S31). The patient test data is received by the POC computer 20 via a POC interface such as a serial interface, a USB interface, an Ethernet interface, a Wi-Fi interface or a Bluetooth® interface and 30 (step S32) and the client application 21 and 31 adds an identifier for the device POC computer 20 and 30, and a unique identifier and name for the POC device to the patient test data. The patient test data is then transmitted over a network interface to the service provider's computer 60. Upon receipt at the service provider's computer 60 the device name is used to identify the device module 621 to implemented to process the patient test data from the POC device. The device module 621 verifies that the data is of the format that was expected for the POC device, parses the patient test data and stores the parsed patient test data in the cache 670 (step S36) and constructs a response to the received patient test data (step S37), which is transmitted to the POC computer and passed to the POC device (steps S38 and S39). Some POC devices send messages before they send the patient test data. The device modules 621 comprise code capable of recognising the messages and sending appropriate responses to their respective POC devices. The parsing performed by the device modules 621 takes the patient test data from the POC device and formats the patient test data according to a test type determined from a test type library on the basis of the POC device name. In other words, each device module 621 is associated with a test type since it is associated with a device type, which can only produce patient test data of a certain test type. More than one device type can be associated with a test type, since different device types could be used to provide a test of the same type e.g. ABC Inc's Blood Monitor is one device type and XYZ's Blood Monitor is another device type but both provide patient test data of the same test type—Blood Test A.

Hence the patient test data in the cache 670 (step S36) comprises incomplete and unverified patient test data which is assigned a unique test identifier.

An operator can use the web page to request a list of all patient tests held in the cache 670 requiring completion and verification from the service provider's computer (step S43). The request will identify the operator by their unique operator identifier. The service provider's computer 60 looks up all patient test data in the cache 670 and returns the test identifier, device name, test type and test date to the POC computer 20 and 30 (step S44). The returned data is displayed at the POC computer enabling the operator to use the web page (user interface) to acknowledge the test that they performed (step S45). In response to the selection by the operator to acknowledge or verify patient test data, the test identifiers for the selected patient tests are sent with the operator identifier and order identifier to the service provider's computer 60 (step S46a) where the operator identifier is associated with the patient test data in the cache 670 (step S47) and the patient test data for the test is stored in the cache 670 with the order identifier and patient identifier (step S53). The application server 62 then identifies fields in the patient test data that are missing for the test type (step S54). The EHR providers set required data fields for patient test data. The application server can obtain this information via the EHR interface 630 and uses this to define required fields in each test type. The required fields in the test type object must include all required fields for all EHR providers for that test type. An HTML form is then generated by the web server 61 in step S55 and transmitted to the POC computer 20 and 30 for display by the web browser 22 and 32 (step S56). The form enables the input or data for the required fields, which can include a field for operator comments or can solely comprise of a field for operator comments. The term required additional data in the context of this invention hence encompasses the provision of comments. However, if the operator decides to add no comments, the requirement for additional data is met by simply returning no comments—the comments data comprises empty data or a null. In this circumstance, the operator has been given the opportunity to comment and has taken the decision that no comments are required. Hence, this effectively comprises information that the operator had no comments to make.

The displayed form can enable an operator to input additional data by free form text, numerals, or by selection of options e.g. by selecting from displayed drop down options. Where the operator can input data, the form can be configured to perform rudimentary known form filling checks e.g. a numeric input can reject non numeric input (step S57). This assists in reducing operator input errors. The user input is then transmitted to the service provider's computer 60, where the data is checked for errors and if no errors are detected the additional data is stored in the cache with the patient test data (step S59). The error checking that can be performed at the service provider's computer is much more sophisticated and can be based on algorithmic rules dependent upon the test type, operator identifier, POC device type etc. The complete patient test data in the cache 670 is then used to generate a patient test data display output in the form of a web page by the web server 61 (step S59) and the web browser 22 and 32 at the POC computer 20 and 30 accesses the web site for display of the complete patient test data (step S60). This enables an operator to select to accept the complete patient test data (step S61), which causes the service provider's computer 60 to send the complete patient test data to the test data database 64 in the data warehouse 600 (step S62). The patient test data is also passed to the EHR interface 630 where the EHR provider to which the patient test data is to be sent is identified from the order identifier and any additional EHR identifier. This identification is used to implement a specific EHR module 631 for the patient test data to be transmitted to the EHR provider. The EHR module 631 has knowledge of the format of the data structure of patient test data in the EHR and can hence parse the patient test data from the test type format common to all patient test data in the service provider's computer 60 to the EHR specific data format or structure. The patient test data is then transmitted to the EHR provider's computer 40 and 50 for storage in the EHR database 43 and 53 associated with the order identifier and the patient identifier.

As can be seen from the description of the operation of the embodiments, the use of the cache for storing the patient test data at the service provider's computer ensures that the patient test data is stored and available for uploading to the EHR provider's computers 40 and 50 and can wait if an EHR provider's computer 40 and 50 becomes unavailable until it becomes available so not patient test data is lost. The patient test data is only stored in the test data database 64 of the data warehouse 600 when the operator has verified the patient test data and the required additional data has been entered and added to the patient test data from the POC device.

Although the embodiments of FIGS. 7a and 7b, 8a and 8b, and 9a and 9b only describe a process in which an operator takes one test so that only one set of patient test data is stored in the cache, the operator is free to take multiple tests with the same POC device or multiple POC devices so that multiple sets of test data are stored in the cache. The operator can then select one at a time or even a group at a time for uploading into the EHR by entering or selecting patient identifiers or name, order identifiers, and test identifiers appropriately.

The data structures used in the processing system of the embodiments of the invention comprise:
POC Facility (Having a POC Facility ID)
POC computer IDs
Operator IDs
EHR IDs and login details
POC Computer (POC Computer ID)
POC device IDs
Operator (Operator ID)
Name
Login details
Mobile telephone number
Test qualification data (instance of a device type)
Quality control qualification data (instance of a device type)
Device Type
Device instances
Device ID
Test Type
Reference ranges per device type
Quality Control Data
POC computer ID
Operator ID
Facility ID
Time and date
Results
Device ID
Device type
Test type
Additional data e.g. comments
Accept or reject my operator (reason input by operator)
Consumable type
Test Data
POC computer ID
Operator ID
Facility ID
Time and date
Results (parsed and original)
Device ID
Device type
Patient ID
Order ID
Additional data e.g. comments
Accept or reject my operator (reason input by operator)
Consumable type Patient test data will comprise some common fields such as patient identifier, data and time of test, test type, and device identifier and some fields that are test specific e.g. for a urinalysis test the data will include data for glucose level and pH. The additional required data to be input by an operator for a urinalysis test can include colour and clarity of the sample. The user interface for such a selection can provide a limited selection of colour and clarity values that the operator has to choose from.

Continuing with the example of a urinalysis, an instantiation of the test type for a specific device would include a Device ID e.g. the serial number and data comprising: pH, glucose concentration, colour, clarity, ketone, blood, nitrite, protein, lucasite esterase, bilurubine and specific gravity.

For quality control and regulatory compliance it is necessary for regular quality control (QC) tests to be performed on the POC devices. Such tests are performed usually on known samples and the tests are performed in the same manner as patient tests except that there is no order identifier or patient identifier to be associated with the QC test data and the test data is not transmitted to the EHR provider. It is just stored in the compliance database 65 in the data warehouse 600 for use in regulatory compliance auditing and for use in applying regulatory compliance restrictions on the taking of patient test data, as will be described with reference to FIG. 8 herein after.

As shown in FIG. 1, the data warehouse 600 includes a device and user database 63. This database stores user login data and device configuration data which can be made available to the client application on the POC computer for the configuration of the client application for new POC devices. The data warehouse 600 also includes a compliance database. This database stored rules required to be complied with to meet regulatory compliance. It also stored the QC test data for the POC devices. It further stores qualification data for the operators, which identifies which POC devices and which test types each operator is qualified to carry out.

One embodiment of the present invention helps POC facilities to be compliant with regulations. A significant regulation is the Clinical Laboratory Improvement Amendments (CLIA) in the US, which was passed by Congress in 1988 establishing standards for all laboratory testing to ensure accuracy, reliability and timeliness of patient test results regardless of where the test was performed.

A physician performing POCT in their offices is considered to have a laboratory and needs a CLIA Certificate of Waiver. A CLIA certificate is also required if the practice wants Medicare money. Once a practice has obtained a CLIA certificate, requirements for testing include allowing unannounced or announced on-site inspections, which can be conducted by representatives of the Department of Health for example. This is serious because failing such an inspection will put Medicare funding at risk and the fear of inspection is a reason why many practices do not conduct their own POCT.

In a study conducted by the states of Colorado and Ohio, it was found that 32% did not perform QC as required by manufacturers, and 19% had personnel who were neither trained nor evaluated for use of the POC devices.

An embodiment of the present invention assists practices remain compliant by facilitating the capture of patient test results only is the correct procedures for compliance have been followed. Part of this procedure requires the capturing of QC results for POC devices and storing the results for compliance checking. The QC data as detailed herein above enables compliance checks to be carried out for each set of patient test data from a POC device. Further, data on the qualifications of operators is required to be input and stored to keep a record of the capabilities and qualifications of POC device operators. The qualification data can include details on the qualifications and training of the operators including defining any on-going training requirements and continued professional learning requirements for example. Hence when a patient test result is input, regulatory compliance with regard to the qualifications of the operator can simply be checked.

Manufacturers QC requirements for POC devices may require operators to run QC tests daily or weekly. A QC test may require a known sample to the tested and the results stored for later comparison. The QC test requirements are stored in the compliance database 65 for the POC devices as well as past QC test data. This enables checks on incoming patient test data to be performed easily to determine whether the patient test is regulatory compliant with regard to the device manufacturers QC test requirements.

POC device manufacturer may specify a cleaning and maintenance routine that must be followed for the POC device. The compliance database 65 stores POC device cleaning and maintenance requirements and recorded data for the cleaning and maintenance carried out by operators or by POC device engineers. Calibration tests are one form of maintenance and may be required to be performed periodically to recalibrate the POC device if necessary. A procedure to recalibrate the POC device is run and the result of the calibration is stored in the compliance database 65. The recalibration results may comprise data on the recalibration changes made to the POC device settings and the new POC device setting.

Figure 10:
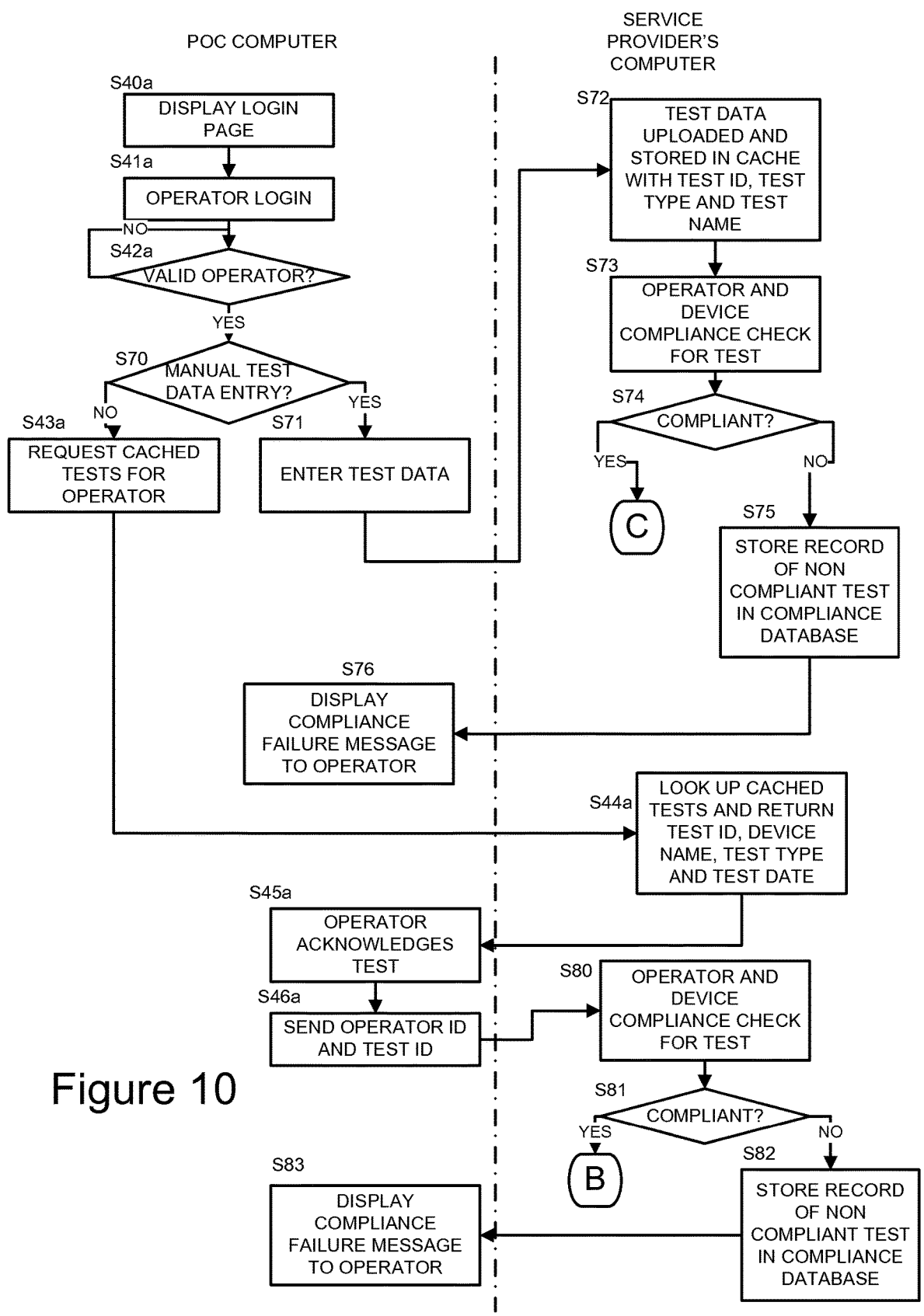
FIG. 10 is a flow diagram illustrating the method of determining regulatory compliance according to one embodiment of the invention.

Referring now to FIG. 10, this diagram is a flow diagram illustrating patient test data processing with regulatory compliance checks regulating the storing of patient test data. The process maps to the process of FIGS. 7a and 7b and hence the same step reference numbers have been used for steps which are the same. This embodiment of the present invention is applicable not just to the automated input of patient test data from POC devices, but also to the manual input of data from POC devices. The compliance process could be used with the method of FIGS. 8a and 8b or 9a and 9b.

In step S40a a POC computer at a POC facility displays a login page such as a web page. The operator enters login data which is validated (steps S41a and S42a) to perform a conventional login procedure based on operator data stored in a user and device database in a service provider's computer. Once logged in, the operator can select to enter patient test data manually or to use automatic POC device data input (step S70). The manual selection may simply take the form of selecting a POC test or POC device that does not support automatic patient test data input.

If manual patient test data is selected, the patient test data is input on an appropriate user interface e.g. a web page served from the web server of the service provider's computer (step S71) and the entered data is transmitted to the service provider's computer, where it is stored in the cache with a unique test identifier, a test type and a test name (step S72). A regulatory compliance check is then performed using the device identifier and the operator identifier for the test type (step S73). Qualification data for the operator is located in the compliance database 65 and it is compared compliance requirements for the POC device and/or test type. The QC data and/or maintenance data for the POC device is located in the compliance database 65 and it is compared with compliance requirements for the POC device. If the patient test data is determined to be compliant (step S74), the patient name or patient identifier that was entered by the operator with the manual data input is transmitted via the service provider's computer to the EHR provider's computer where the data is received (step S49 in FIG. 7a). The process then continues as in the embodiment of FIGS. 7a and 7b from step S49.

If the patient test data is determined not to be compliant (step S74), a record of the non-compliance is stored in the compliance database 65 (step S75) and a message is returned to the POC computer for display to the operator to inform them of the compliance failure for the patient test (step S76).

If automatic patient test data input is selected (step S70), an operator can use a web page to request a list of all patient tests held in the cache 670 requiring completion and verification from the service provider's computer (step S43a). The request will identify the operator by their unique operator identifier. The service provider's computer 60 looks up all patient test data in the cache 670 and returns the test identifier, device name, test type and test date to the POC computer 20 and 30 (step S44a). The returned data is displayed at the POC computer enabling the operator to use the web page (user interface) to acknowledge the test that they performed (step S45a). In response to the selection by the operator to acknowledge or verify patient test data, the test identifiers for the selected patient tests are sent with the operator identifier to the service provider's computer 60 (step S46a). A regulatory compliance check is then performed using the device identifier and the operator identifier for the test type (step S80). Qualification data for the operator is located in the compliance database 65 and it is compared compliance requirements for the POC device and/or test type. The QC data and/or maintenance data for the POC device is located in the compliance database 65 and it is compared with compliance requirements for the POC device. If the patient test data is determined to be compliant (step S81), the operator identifier is associated with the patient test data in the cache 670 (step S47 of FIG. 7a). The process then continues as for the embodiment of FIGS. 7a and 7b from step S47.

If the patient test data is determined not to be compliant (step S81), a record of the non-compliance is stored in the compliance database 65 (step S82) and a message is returned to the POC computer for display to the operator to inform them of the compliance failure for the patient test (step S83). Hence in this embodiment the patient test data is prevented from being uploaded to the EHR.

Figure 7A:
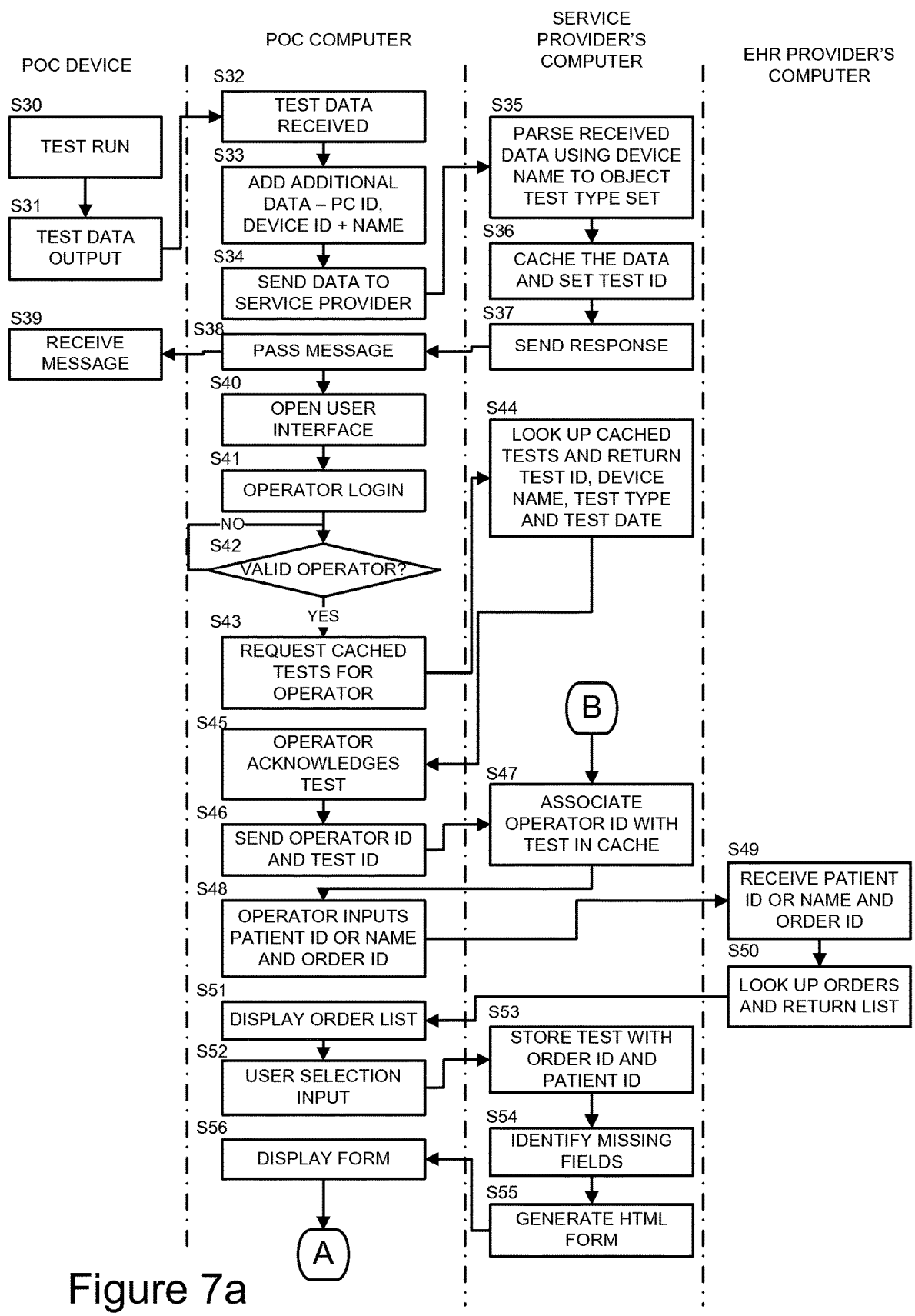
FIGS. 7a and 7b are a flow diagram illustrating the method of processing patient test data according to one embodiment of the invention.
Figure 7B:
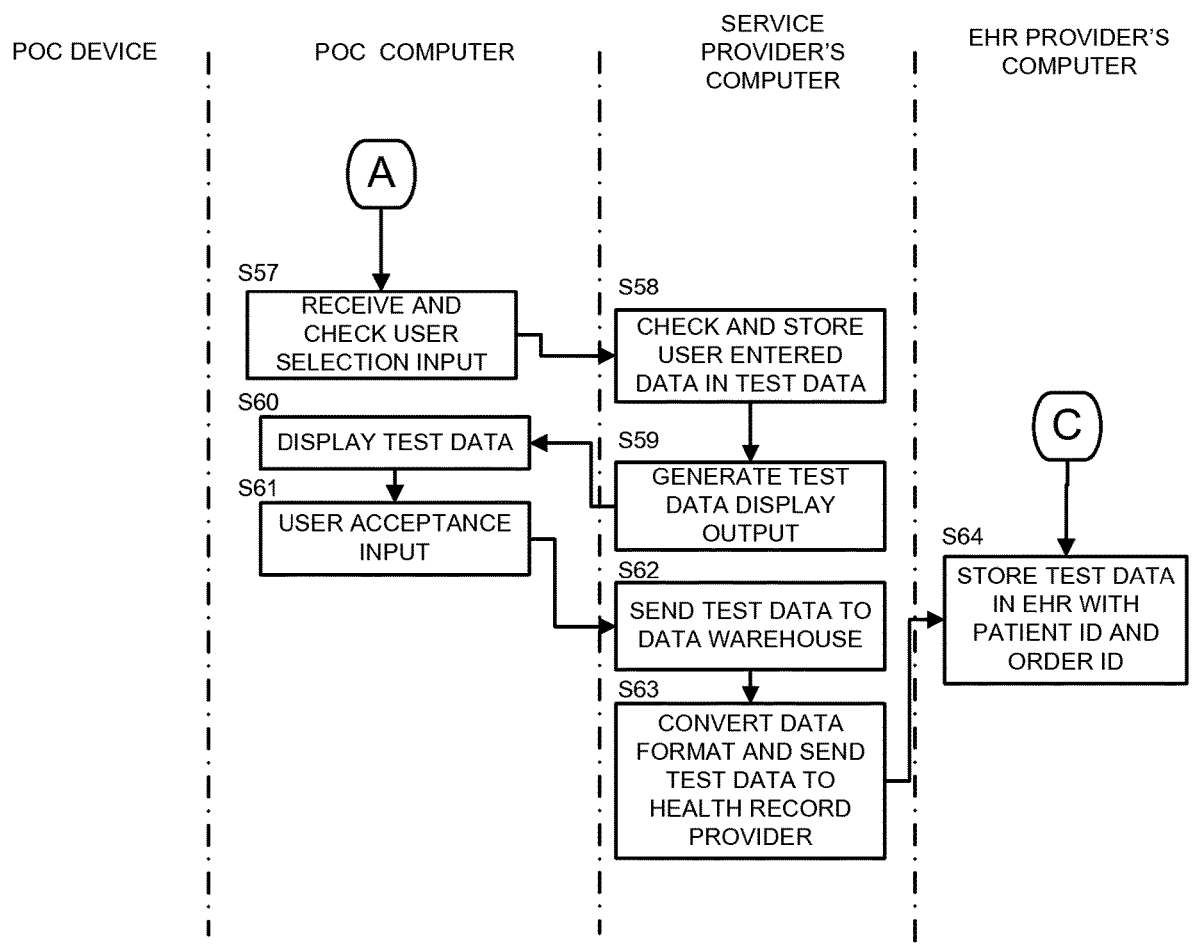

In an alternative embodiment, when non-compliance is determined, the patient test data is simply flagged as non-compliant and in addition to the storage of the record on non-compliance in the compliance database, the non-compliant patient test data can be processed in the same manner as from step S47 in FIG. 7a. Hence in this embodiment, the patient test data is not prevented form being uploaded into the EHR but is clearly marked or flagged as failing the compliance check.

It can hence be seen from this embodiment that the process of patient test data recording in an EHR can be readily controlled to ensure that regulatory compliance requirements are met by POC facilities.

In the described embodiments of the invention, the provision of the data warehouse 600 enables centralise and common detailed reports on patient tests for multiple EHR providers, POC devices, operators, POC facilities, test types, regulatory compliance, and even POC consumable user for POC devices from the same manufacturer or supplier.

It will be readily understood to those skilled in the art that various other changes in the details, material, and arrangements of the parts and method stages which have been described and illustrated in order to explain the nature of the inventive subject matter may be made without departing from the principles and scope of the inventive subject matter as expressed in the subjoined claims.

What is claimed is:

1. A point of care computer comprising:
   a device interface to receive patient test data for a medical test performed on a patient using a point of care device from the point of care device, and to perform device specific processing on the received patient test data by parsing the received patient test data to identify a device type from the received patient test data, and reformatting the received patient test data according to a test type identified from a library of test types using the identified device type;
   a network interface to transmit the reformatted patient test data to a remote server system over a network and to receive data identifying additional required data to complete the patient test data from the remote server system over the network; and
   an operator interface to process the received data identifying additional required data, to automatically generate for display a form including fields requiring an operator to input the additional required data, and to receive the additional required data as operator input data in response to form filling by the operator;

wherein the network interface is to transmit the operator input data to the remote server system over the network.

2. A point of care computer according to claim 1, including a processor module to add point of care computer identifier data and device identifier data to the patient test data, wherein the network interface is to transmit the patient test data including the added point of care identifier to the remote server system.

3. A point of care computer according to claim 2, wherein the processor is to determine the device identifier data dependent upon parameters for the device interface.

4. A point of care computer according to claim 1, wherein the operator interface is to receive operator identification information and the network interface is to transmit the received operator identification information to the server system for the association of operator identifier data with the patient test data.

5. A point of care computer according to claim 1, wherein the operator interface is to check the received operator input data for input errors.

6. A point of care computer according to claim 1, wherein the network interface is to receive complete patient test data comprising the patient test data and the operator input data from the server system, to display the complete patient test data and to receive an operator response input.

7. A server system for processing patient test data from at least one point of care device, the server system comprising:
a memory storing electronic health record provider requirements;
a point of care interface to receive patient test data for a medical test performed on a patient using a point of care device from a point of care computer over a network, the point of care computer to receive the patient test data from at least one point of care device;
a processor to perform device specific processing on the received patient test data by parsing the received patient test data to identify a device type from the received patient test data, and reformatting the received patient test data according to a test type identified from a library of test types using the identified device type and to process the reformatted patient test data using the electronic health record provider requirements stored in the memory to automatically identify additional required data missing from the patient test data to complete the patient test data;
wherein the point of care interface is further to transmit, to the point of care computer over the network, data identifying the additionally required data to be input by an operator using an operator interface to complete the patient test data, and further to receive the additional required data as operator input data from the point of care computer over the network;
wherein the processor is further to process the patient test data to add the received operator input data to the patient test data to form complete patient test data; and
an electronic health record interface to receive, from one or more electronic health record providers computers over the network, the electronic health record provider requirements and store the electronic health record provider requirements in the memory and to transmit the formed complete patient test data to at least one of the one or more electronic health record providers computers over the network.

8. A server system according to claim 7, wherein the processor is to convert the received patient test data to a structure common to patient test data from a plurality of point of care devices.

9. A server system according to claim 8, wherein the processor is to convert the received patient test data in the structure common to patient test data from a plurality of point of care devices into a structure specific to one of a plurality of electronic health record providers.

10. A server system according to claim 7, wherein the point of care interface is to receive operator information, and the processor is to derive and associate operator identifier data with the patient test data.

11. A server system according to claim 7, including a cache memory for storing the patient test data until the complete patient test data is formed.

12. A server system according to claim 7, wherein the processor is to check the received patient test data and operator input data for errors.

13. A server system according to claim 7, wherein the point of care interface is to transmit the complete patient test data to the point of care computer for display to the operator, and to receive an operator response input.

14. A method of operating a point of care computer, the method comprising:
receiving patient test data for a medical test performed on a patient using a point of care device, from the point of care device using a device interface, the patient test data comprising data in one of a plurality of device dependent formats;
performing device specific processing on the received patient test data by parsing the received patient test data to identify a device type from the received patient test data;
reformatting the received patient test data according to a test type identified from a library of test types using the identified device type;
transmitting the reformatted patient test data to a remote server system over a network using a network interface,
receiving data identifying additional required data to complete the patient test data from the remote server over the network using the network interface;
processing the received data identifying additional required data and automatically generating and displaying on a display a form including fields requiring an operator to input the additional required data;
receiving the additional required data as operator input data in response to form filling by the operator using a user input device; and
transmitting the operator input data to the server system over the network using the network interface.

15. A method according to claim 14, including adding point of care computer identifier data and device identifier data to the patient test data for transmission to the remote server system using the network interface.

16. A method according to claim 15, including determining the device identifier data dependent upon parameters for the device interface.

17. A method according to claim 14, including receiving operator identification information from the user input device for transmission by the network interface to the remote server system for the association of operator identifier data with the patient test data.

18. A method according to claim 14, including checking the received operator input data for input errors.

19. A method according to claim 14, including receiving complete patient test data over the network using the network interface, the complete patient test data comprising the patient test data and the operator input data, displaying on the display the complete patient test data, and receiving an operator response input from the user input device.

20. A method of operating a server system to process patient test data from at least one point of care device, the method comprising:

receiving, from one or more electronic health record providers computers over a network, electronic health recorder provider requirements and storing the electronic health record provider requirements in a memory using an electronic health record interface;

receiving patient test data for a medical test performed on a patient using a point of care device from a point of care computer over the network using a point of care interface, the point of care computer to receive the patient test data from at least one point of care device;

performing device specific processing on the received patient test data by parsing the received patient test data to identify a device type from the received patient test data;

reformatting the received patient test data according to a test type identified from a library of test types using the identified device type;

processing the reformatted patient test data using the electronic health record provider requirements stored in the memory to automatically identify additional required data missing from the patient test data to complete the patient test data;

using the point of care interface to transmit, to the point of care computer over the network data identifying the additional required data to be input by an operator of the point of care computer using an operator interface to complete the patient test data;

receiving the additional required data as operator input data from the point of care computer over the network;

processing the patient test data to add the operator input data to the patient test data to form and store complete patient test data; and transmitting the formed complete patient test data to at least one of the one or more electronic health record providers computers over the network using the electronic health record interface.

21. A method according to claim 20, including converting the received patient test data to a structure common to patient test data from a plurality of point of care devices.

22. A method according to claim 21, including converting the received patient test data in the structure common to patient test data from a plurality of point of care devices into a structure specific to one of a plurality of electronic health record providers.

23. A method according to claim 20, including receiving operator information over the point of care interface, and deriving and associating operator identifier data with the patient test data.

24. A method according to claim 20, including storing the patient test data in a cache memory until the complete patient test data is formed.

25. A method according to claim 20, including checking the received patient test data and operator input data for errors.

26. A method according to claim 20, including transmitting the complete patient test data to the point of care computer for display to the operator, and receiving an operator response input using the point of care interface.

* * * * *